(12) United States Patent
Guo et al.

(10) Patent No.: US 12,286,659 B2
(45) Date of Patent: Apr. 29, 2025

(54) TANDEM DNA ELEMENT CAPABLE OF ENHANCING PROTEIN SYNTHESIS EFFICIENCY

(71) Applicant: KANGMA-HEALTHCODE (SHANGHAI) BIOTECH CO., LTD., Shanghai (CN)

(72) Inventors: Min Guo, Shanghai (CN); Zijian Zhou, Shanghai (CN); Xue Yu, Shanghai (CN)

( * ) Notice: Subject to any disclaimer, the term of this patent is extended or adjusted under 35 U.S.C. 154(b) by 935 days.

(21) Appl. No.: 16/766,079

(22) PCT Filed: Nov. 30, 2017

(86) PCT No.: PCT/CN2017/113941
§ 371 (c)(1),
(2) Date: May 21, 2020

(87) PCT Pub. No.: WO2019/100431
PCT Pub. Date: May 31, 2019

(65) Prior Publication Data
US 2023/0203555 A1    Jun. 29, 2023

(30) Foreign Application Priority Data
Nov. 24, 2017 (CN) .......................... 201711194355.9

(51) Int. Cl.
C12P 21/00 (2006.01)
C12N 15/67 (2006.01)
C12N 15/81 (2006.01)

(52) U.S. Cl.
CPC .............. *C12P 21/00* (2013.01); *C12N 15/81* (2013.01); *C12N 2800/102* (2013.01); *C12N 2840/203* (2013.01)

(58) Field of Classification Search
None
See application file for complete search history.

(56) References Cited

U.S. PATENT DOCUMENTS 9,528,137 B2 * 12/2016 Jewett ..................... C12P 19/34

FOREIGN PATENT DOCUMENTS

| WO | WO2011/028914 | * 10/2011 |
| WO | WO2014/144583 | * 9/2014 |

* cited by examiner

*Primary Examiner* — Suzanne M Noakes
*Assistant Examiner* — Jae W Lee
(74) *Attorney, Agent, or Firm* — Clement Cheng

(57) ABSTRACT

A tandem DNA element capable of enhancing protein synthesis efficiency, in particular, the nucleic acid construct is formed by an IRES enhancer (such as ScBOI1, ScFLO8, ScNCE102, ScMSN1, KlFLO8, KlNCE102, KlMSN1, KlBOI1) derived from eukaryotic cells (such as yeast), a Ω sequence, and a yeast-specific Kozak sequence in tandem. The use of the nucleic acid construct in a yeast-based in vitro biosynthesis system (such as a yeast-based in vitro protein synthesis system) can significantly improve protein synthesis efficiency.

11 Claims, 4 Drawing Sheets
Specification includes a Sequence Listing.

A

B

TANDEM DNA ELEMENT CAPABLE OF ENHANCING PROTEIN SYNTHESIS EFFICIENCY

The specification incorporates by reference 14_Sequence_Listing_txt.txt created May 21, 2020, having a file size of 23 kB, submitted with the original filing.

BACKGROUND OF THE INVENTION

1. Technical Field

The present invention relates to the field of biotechnology, and more particularly, to a tandem DNA element capable of enhancing protein synthesis efficiency.

2. Description of the Related Art

Proteins are important molecules in cells and are involved in almost all functions of cells. The sequence and structure of proteins determine the function thereof. In cells, proteins can act as enzymes to catalyze various biochemical reactions and can act as signaling molecules to coordinate various activities of organisms. Proteins can support biological forms, can store energy, can transport molecules, and can enable organisms to move. In the field of biomedicine, antibodies (a kind of protein), as targeted drugs, are an important means to treat cancer and other diseases.

In cells, the regulation of protein translation plays an important role not only in responding to external pressures such as nutritional deficiency but also in various processes such as cell development and differentiation. Four processes of protein translation include translation initiation, translation elongation (translation extension), translation termination and ribosome recycling, among which translation initiation is the most regulated process. There are two ways of translation initiation in eukaryotic cells: the traditional cap-dependent way and the cap-independent way (as shown in FIG. 1).

The "cap structure" dependent translation initiation is a very complicated process involving dozens of translation initiation factors and the 40S small subunit of the ribosome. The "cap structure" independent translation initiation is mainly mediated by Internal Ribosome Entry Sites (IRESs) located in the 5'-untranslated region of mRNA. IRESs were first discovered in viral mRNAs in the 1980s, and endogenous IRESs in cells were also widely reported later. Viral IRESs usually have complex secondary and tertiary structures. Within the host cell, viral IRESs recruit ribosomes of the host cell to initiate protein translation, dependent on or independent of the host cell's translation initiation factors. Compared with viral IRESs, endogenous IRESs in cells usually have a lower efficiency of initiating protein translation which is regulated by a variety of complex mechanisms that do not have commonality. Different endogenous IRESs in cells do not have commonality in sequence and structure, which makes it difficult to be predicted.

In addition to the above understanding of intracellular protein synthesis, protein synthesis can also be performed outside the cell. An in vitro protein synthesis system generally refers to a lysis system based on bacteria, fungi, plant cells or animal cells, which is added with components including mRNA or DNA template, RNA polymerase, amino acids and ATP to complete rapid and efficient translation of exogenous proteins. Currently, frequently used commercial in vitro protein expression systems include E. coli extract (ECE) systems, rabbit reticulocyte lysate (RRL) systems, wheat germ extract (WGE) systems, insect cell extract (ICE) systems and human source systems.

The mRNA synthesized in vitro usually does not have a "cap structure", and modification of the mRNA with a "cap structure" is time-consuming and expensive. As a result, the in vitro protein synthesis system generally uses a cap-independent translation initiation method for protein synthesis. However, the efficiency of translation initiation using only IRES or Ω sequence is rather low, and the purpose of rapid, efficient and high-throughput protein synthesis in vitro cannot be achieved. At present, there is no research on the concatenation of these two types of translation initiation elements in tandem.

Therefore, there remains an urgent need in the art for developing a new nucleic acid construct capable of enhancing protein synthesis efficiency, which concatenates the IRES sequence and the Ω sequence in tandem.

SUMMARY OF THE INVENTION

One purpose of the present invention is to provide a new nucleic acid construct capable of enhancing the efficiency of protein translation, which concatenates an IRES sequence and Ω sequence in tandem.

According to the first aspect, the present invention provides a nucleic acid construct, comprising a nucleic acid sequence of Formula I:

$$Z1\text{-}Z2\text{-}Z3\text{-}Z4\text{-}Z5 \tag{I}$$

wherein,

Z1~Z5 are respectively an element as part of the construct;

each "-" is independently a bond or a nucleotide linking sequence;

Z1 is an enhancer element, and the enhancer element comprises an IRES element;

Z2 is a 5' leading sequence of tobacco mosaic virus, that is Ω sequence;

Z3 is an oligomeric chain of adenine deoxynucleotide, and also represented by $[oligo(A)]_n$;

Z4 is a translation initiation codon;

Z5 is a serine codon;

wherein, Z3, Z4 and Z5 constitute a Kozak sequence, and the Kozak sequence is derived from yeast.

In another preferred embodiment, Z1 is derived from yeast.

In another preferred embodiment, the source of the IRES element is one or more types of cells selected from the group consisting of a prokaryotic cell and a eukaryotic cell.

In another preferred embodiment, the eukaryotic cell includes higher eukaryotic cells.

In another preferred embodiment, the IRES element includes an endogenous IRES element and an exogenous IRES element.

In another preferred embodiment, the source of the IRES element is one or more types of cells selected from the group consisting of human cell, Chinese hamster ovary (CHO) cell, insect cell, wheat germ cell and rabbit reticulocyte.

In another preferred embodiment, the IRES element is selected from the group consisting of ScBOI1, ScFLO8, ScNCE102, ScMSN1, KlFLO8, KlNCE102, KlMSN1, KlBOI1 and combinations thereof.

In another preferred embodiment, the yeast is selected from the group consisting of Saccharomyces cerevisiae, Kluyveromyces and a combination thereof.

In another preferred embodiment, the *Kluyveromyces* is selected from the group consisting of *Kluyveromyces lactis, Kluyveromyces marxianus, Kluyveromyces dobzhanskii* and combinations thereof.

In another preferred embodiment, the translation initiation codon is selected from the group consisting of ATG, ATA, ATT, GTG, TTG and combinations thereof.

In another preferred embodiment, the translation initiation codon is ATG.

In another preferred embodiment, the serine codon is selected from the group consisting of TCT, TCC, TCA, TCG, AGT, AGC and combinations thereof.

In another preferred embodiment, the serine codon is TCT.

In another preferred embodiment, n is in the range of 6-12, preferably, in the range of 8-10.

In another preferred embodiment, the $\Omega$ sequence includes direct repeat modules $(ACAATTAC)_m$ and $(CAA)_p$.

In another preferred embodiment, m is in the range of 1-6, preferably, in the range of 2-4.

In another preferred embodiment, p is in the range of 6-12, preferably, in the range of 8-10.

In another preferred embodiment, the number of the $(CAA)_p$ module is in the range of 1-5, preferably, in the range of 1-3.

In another preferred embodiment, the $(CAA)_p$ module further includes optimized $(CAA)_p$ modules.

In another preferred embodiment, the Kozak sequence is shown in SEQ ID NO.: 84.

In another preferred embodiment, the sequence of the nucleic acid construct can be any one of SEQ ID NO.: 2-17.

In another preferred embodiment, the sequence of the nucleic acid construct can be any one of SEQ ID NO.: 2-9.

In another preferred embodiment, the sequence of the nucleic acid construct is SEQ ID NO.: 3, 4 or 6.

According to the second aspect, the present invention provides a nucleic acid construct, comprising a structure of Formula II from 5' to 3':

$$Z1\text{-}Z2\text{-}Z3\text{-}Z4\text{-}Z5\text{-}Z6 \qquad (II)$$

wherein,

Z1~Z6 are respectively an element as part of the nucleic acid construct;

each "-" is independently a bond or a nucleotide linking sequence;

Z1 is an enhancer element, and the enhancer element comprises an IRES element;

Z2 is a 5' leading sequence of tobacco mosaic virus, that is $\Omega$ sequence;

Z3 is an oligomeric chain of adenine deoxynucleotide, and also represented by $[oligo(A)]_n$;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

In another preferred embodiment, the coding sequence of the exogenous protein is derived from a prokaryote or a eukaryote.

In another preferred embodiment, the coding sequence of the exogenous protein is derived from animal, plant or pathogen.

In another preferred embodiment, the coding sequence of the exogenous protein is derived from mammal, preferably primate or rodent, including human, mouse and rat.

In another preferred embodiment, the coding sequence of the exogenous protein encodes an exogenous protein selected from the group consisting of luciferin, luciferases (such as firefly luciferase), green fluorescent protein, yellow fluorescent protein, aminoacyl-tRNA synthetase, glyceraldehyde-3-phosphate dehydrogenase, catalase, actin, variable regions of antibodies, luciferase mutants, $\alpha$-amylase, enterocin A, hepatitis C virus (HCV) E2 glycoprotein, insulin precursors, interferon $\alpha$A, interleukin-1$\beta$, lysozyme, serum albumins, single-chain variable fragment (scFv) of antibodies, transthyretin, tyrosinase, xylanase and combinations thereof.

In another preferred embodiment, the exogenous protein is selected from the group consisting of luciferin, luciferases (such as firefly luciferase), green fluorescent protein, yellow fluorescent protein, aminoacyl-tRNA synthetase, glyceraldehyde-3-phosphate dehydrogenase, catalase, actin, variable regions of antibodies, luciferase mutants, $\alpha$-amylase, enterocin A, hepatitis C virus (HCV) E2 glycoprotein, insulin precursors, interferon $\alpha$A, interleukin-1$\beta$, lysozyme, serum albumins, single-chain variable fragment (scFv) of antibodies, transthyretin, tyrosinase, xylanase and combinations thereof.

In another preferred embodiment, the sequence of the nucleic acid construct can be any one of SEQ ID NO.: 85-87.

According to the third aspect, the present invention provides a nucleic acid construct, comprising a structure of Formula III from 5' to 3':

$$Z0\text{-}Z1\text{-}Z2\text{-}Z3\text{-}Z4\text{-}Z5\text{-}Z6 \qquad (III)$$

wherein,

Z0~Z6 are respectively an element as part of the nucleic acid construct;

each "-" is independently a bond or a nucleotide linking sequence;

Z0 is a promoter element, and the promoter element is selected from the group consisting of T7 promoter, T3 promoter, SP6 promoter and combinations thereof;

Z1 is an enhancer element, and the enhancer element comprises an IRES element;

Z2 is a 5' leading sequence of tobacco mosaic virus, that is $\Omega$ sequence;

Z3 is an oligomeric chain of adenine deoxynucleotide, and also represented by $[oligo(A)]_n$;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

According to the fourth aspect, the present invention provides a nucleic acid construct comprising a structure of Formula IV from 5' to 3':

$$Z0'\text{-}Z1\text{-}Z2\text{-}Z3\text{-}Z4\text{-}Z5\text{-}Z6 \qquad (IV)$$

wherein,

Z0'~Z6 are respectively an element as part of the construct;

each "-" is independently a bond or a nucleotide linking sequence;

Z0' is GAA;

Z1 is an enhancer element, and the enhancer element comprises an IRES element;

Z2 is a 5' leading sequence of tobacco mosaic virus, that is $\Omega$ sequence;

Z3 is an oligomeric chain of adenine deoxynucleotide, and also represented by $[oligo(A)]_n$;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

According to the fifth aspect, the present invention provides a vector or a vector combination, wherein, the vector or the vector combination contains the nucleic acid construct according to the first aspect to the fourth aspect of the present invention.

According to the sixth aspect, the present invention provides a genetically engineered cell, wherein, the genetically engineered cell has the nucleic acid construct according to the first aspect to the fourth aspect of the present invention integrated in its genome at one or more sites, or the genetically engineered cell contains the vector or the vector combination according to the fifth aspect of the present invention.

In another preferred embodiment, the genetically engineered cell includes a prokaryotic cell and a eukaryotic cell.

In another preferred embodiment, the eukaryotic cell includes higher eukaryotic cells.

In another preferred embodiment, the genetically engineered cell is selected from the group consisting of human cell (e.g. Hela cell), Chinese hamster ovary cell, insect cell, wheat germ cell, rabbit reticulocyte, yeast cell and combinations thereof.

In another preferred embodiment, the genetically engineered cell is yeast cell.

In another preferred embodiment, the yeast cell is selected from the group consisting of *Saccharomyces cerevisiae, Kluyveromyces*, and a combination thereof.

In another preferred embodiment, *Kluyveromyces* is selected from the group consisting of *Kluyveromyces lactis, Kluyveromyces marxianus, Kluyveromyces dobzhanskii* and combinations thereof.

According to the seventh aspect, the present invention provides a kit, wherein, the kit comprises reagents selected from one or more of the following groups:
(a) the nucleic acid construct according to the first aspect to the fourth aspect of the present invention;
(b) the vector or the vector combination according to the fifth aspect of the present invention; and
(c) the genetically engineered cell according to the sixth aspect of the present invention.

In another preferred embodiment, the kit further comprises (d) a eukaryote-based in vitro biosynthesis system (such as a eukaryote-based in vitro protein synthesis system).

In another preferred embodiment, the eukaryote-based in vitro biosynthesis system is selected from the group consisting of a yeast-based in vitro biosynthesis system, a Chinese hamster ovary cell based in vitro biosynthesis system, an insect cell based in vitro biosynthesis system, a Hela cell based in vitro biosynthesis system, and combinations thereof.

In another preferred embodiment, the eukaryote-based in vitro biosynthesis system includes a eukaryote-based in vitro protein synthesis system.

In another preferred embodiment, the eukaryote-based in vitro protein synthesis system is selected from the group consisting of a yeast-based in vitro protein synthesis system, a Chinese hamster ovary cell based in vitro protein synthesis system, an insect cell based in vitro protein synthesis system, a Hela cell based in vitro protein synthesis system, and combinations thereof.

In another preferred embodiment, the kit further comprises (e) a yeast-based in vitro biosynthesis system (such as a yeast-based in vitro protein synthesis system).

In another preferred embodiment, the yeast-based in vitro biosynthesis system (such as a yeast-based in vitro protein synthesis system) is a *Kluyveromyces*-based in vitro biosynthesis system (such as a *Kluyveromyces*-based in vitro protein synthesis system), preferably a *Kluyveromyces lactis* based in vitro biosynthesis system (such as a *Kluyveromyces lactis* based in vitro protein synthesis system).

According to the eighth aspect, the present invention provides the use of the nucleic acid construct according to the first aspect to the fourth aspect of the present invention, the vector or the vector combination according to the fifth aspect of the present invention, and the genetically engineered cell according to the sixth aspect of the present invention or the kit according to the seventh aspect of the present invention, which is applicable for high-throughput in vitro protein synthesis.

According to the ninth aspect, the present invention provides an in vitro high-throughput method for exogenous protein synthesis, comprising the following steps:
(i) in the presence of a eukaryote-based in vitro biosynthesis system, providing the nucleic acid construct according to the first aspect to the fourth aspect of the present invention; and
(ii) under suitable conditions, incubating the eukaryote-based in vitro biosynthesis system of step (i) for a period of time T1 to synthesize the exogenous protein.

In another preferred embodiment, the method further comprises:
(iii) optionally isolating or detecting the exogenous protein from the eukaryote-based in vitro biosynthesis system.

In another preferred embodiment, the eukaryote-based in vitro biosynthesis system is a yeast-based in vitro biosynthesis system (such as a yeast-based in vitro protein synthesis system).

In another preferred embodiment, the yeast-based in vitro biosynthesis system (such as a yeast-based in vitro protein synthesis system) is a *Kluyveromyces* based in vitro biosynthesis system (such as a *Kluyveromyces* based in vitro protein synthesis system), preferably a *Kluyveromyces lactis* based in vitro biosynthesis system (such as a *Kluyveromyces lactis* based in vitro protein synthesis system).

In another preferred embodiment, the coding sequence of the exogenous protein is derived from a prokaryote or a eukaryote.

In another preferred embodiment, the coding sequence of the exogenous protein is derived from animal, plant or pathogen.

In another preferred embodiment, the coding sequence of the exogenous protein is derived from mammal, preferably primate or rodent, including human, mouse and rat.

In another preferred embodiment, the coding sequence of the exogenous protein encodes an exogenous protein which is selected from the group consisting of luciferin, luciferases (such as firefly luciferase), green fluorescent protein, yellow fluorescent protein, aminoacyl-tRNA synthetase, glyceraldehyde-3-phosphate dehydrogenase, catalase, actin, variable regions of antibodies, luciferase mutants, α-amylase, enterocin A, hepatitis C virus E2 glycoprotein, insulin precursors, interferon αA, interleukin-1β, lysozyme, serum albumins, single-chain variable fragment (scFv) of antibodies, transthyretin, tyrosinase, xylanase, and combinations thereof.

In another preferred embodiment, the exogenous protein is selected from the group consisting of luciferin, luciferases (such as firefly luciferase), green fluorescent protein, yellow fluorescent protein, aminoacyl-tRNA synthetase, glyceraldehyde-3-phosphate dehydrogenase, catalase, actin, variable regions of antibodies, luciferase mutants, alpha-amylase, enterocin A, hepatitis C virus E2 glycoprotein, insulin precursors, interferon αA, interleukin-1β, lysozyme, serum albumins, single-chain variable fragment (scFv) of antibodies, transthyretin, tyrosinase, xylanase, and combinations thereof.

In another preferred embodiment, in the step (ii), the reaction temperature is in the range of 20-37° C., preferably, in the range of 22-35° C.

In another preferred embodiment, in the step (ii), the reaction time is in the range of 1-10 hours, preferably, in the range of 2-8 hours.

It should be understood that, within the scope of the present invention, the abovementioned technical features and the technical features specifically described in the following (e.g. embodiments or examples) in the present invention can be combined with each other, thereby forming new or preferred technical solutions. Due to space limitations, no more tautology here.

DETAILED DESCRIPTION

After extensive and in-depth research, through a lot of screening and exploration, a new nucleic acid construct that can enhance the efficiency of in vitro protein translation was unexpectedly found for the first time. The nucleic acid construct of the present invention is built by concatenating IRES enhancers (e.g., ScBOI1, ScFLO8, ScNCE102, ScMSN1, KlFLO8, KlNCE102, KlMSN1, KlBOI1) derived from eukaryotic cells (e.g., yeast), the Ω sequence and yeast-specific (e.g., *Kluyveromyces*, preferably *Kluyveromyces lactis*) Kozak sequences. When the nucleic acid construct of the present invention is used in a yeast-based in vitro biosynthesis system (e.g. a yeast-based in vitro protein synthesis system), the relative light unit (RLU) value for indicating the activity of the synthesized luciferase is very high, and can reach 1.65 times that of a tandem sequence (Ω-10A) concatenated by the single Ω sequence and a Kozak sequence, or can be approximately equivalent to that of Ω-10A.

Figure 5:
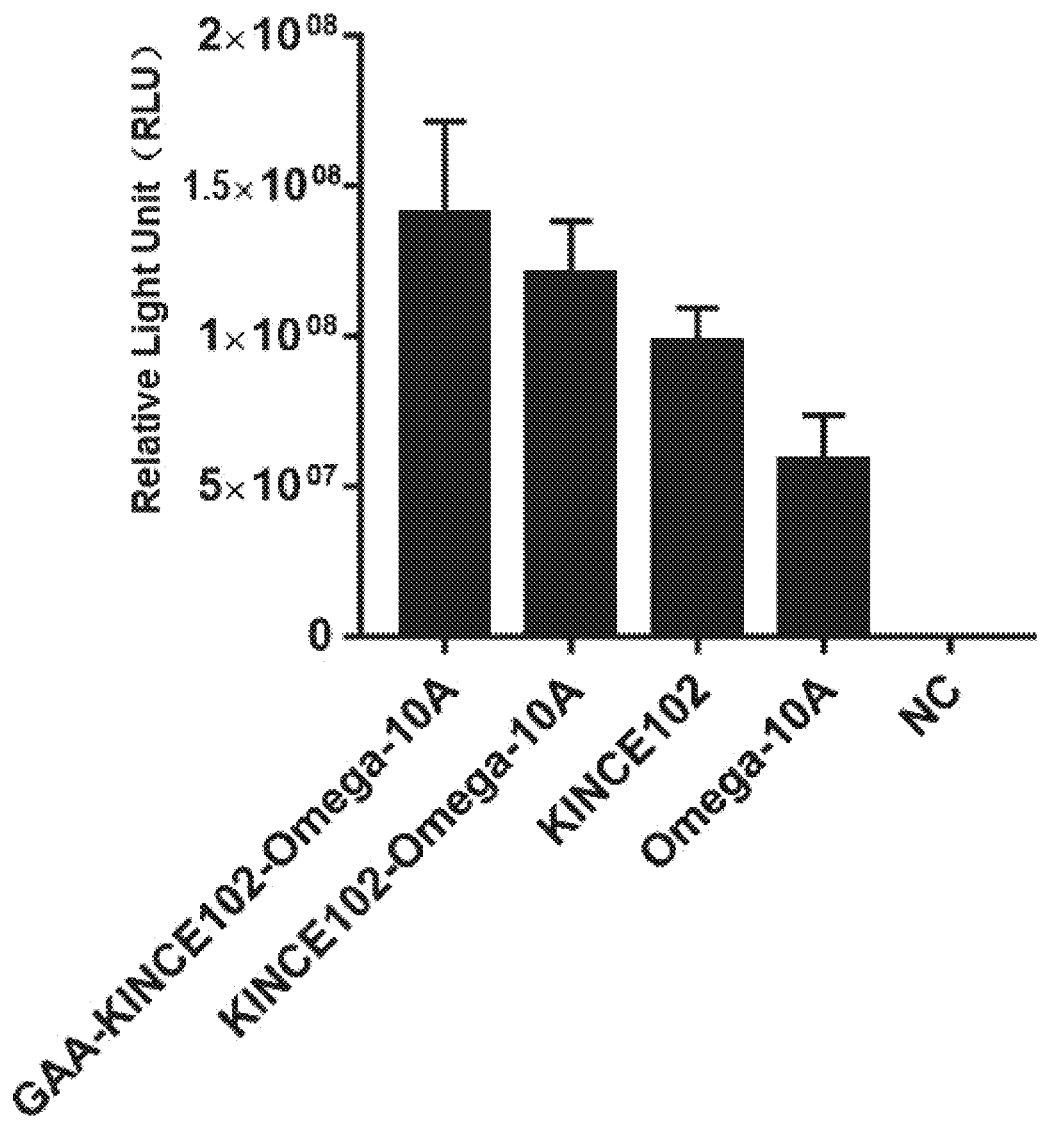
FIG. 5 shows that the Ω-10A sequence and the GAA sequence enhanced the in vitro protein translation efficiency of KlNCE102. The in vitro translation efficiency of the KlNCE102-Ω-10A tandem element was 1.23 times that of KlNCE102, and the in vitro translation efficiency of GAA-KlNCE102-Ω-10A tandem element was 1.28 times that of KlNCE102-Ω-10A, and 2.52 times that of Ω-10A.

In addition, the inventors also surprisingly found that placing three residues of GAA upstream of the nucleic acid construct of the present invention can also enhance the efficiency of protein synthesis, and the relative light unit value of luciferase when using the nucleic acid construct of the present invention to mediate the in vitro synthesis, was increased by approximately 0.28 folds (GAA-KlNCE102-Ω-10A relative to KlNCE102-Ω-10A). In comparison with using Ω-10A, the relative light unit value of luciferase when using GAA-KlNCE102-Ω-10A was increased by 1.52 folds (i.e., the relative light unit value when using GAA-KlNCE102-Ω-10A was 2.52-folds of that when using Ω-10A) (as shown in FIG. 5). Based on the above, the inventors have completed the present invention.

Eukaryote-Based In Vitro Biosynthesis System

The eukaryote-based in vitro biosynthesis system is a transcription-translation coupled system based on eukaryotic cells, which can synthesize RNA starting from DNA template or use DNA or RNA as template to complete protein synthesis in vitro. The eukaryotic cells include yeast cells, rabbit reticulocytes, wheat germ cells, insect cells, human cells and the like. The eukaryote-based in vitro biosynthesis system has advantages of being able to synthesize RNA or proteins with complex structures, of post-translational modification of proteins, etc.

In the present invention, the eukaryote-based in vitro biosynthesis system is not particularly limited. A preferred eukaryote-based in vitro biosynthesis system includes a yeast-based in vitro biosynthesis system, preferably, a yeast-based in vitro protein synthesis system, more preferably, a *Kluyveromyces*-based expression system (more preferably, a *Kluyveromyces lactis* based expression system).

Yeast has advantages of simple culture, efficient protein folding and post-translational modification. Among yeasts, *Saccharomyces cerevisiae* and *Pichia pastoris* are model organisms that express complex eukaryotic proteins and membrane proteins. Yeast can also be used as a raw material for the preparation of in vitro translation systems.

*Kluyveromyces* is an ascosporogenous yeast. Among *Kluyveromyces*, *Kluyveromyces marxianus* and *Kluyveromyces lactis* are yeasts widely used in industry. Compared with other yeasts, *Kluyveromyces lactis* has many advantages, such as super secretion ability, better large-scale fermentation characteristics, conforming to food safety level, the ability of post-translational modification of proteins, and the like.

In the present invention, the eukaryote-based in vitro biosynthesis system comprises:
 (a) a eukaryotic cell extract;
 (b) polyethylene glycol;
 (c) optional exogenous sucrose; and
 (d) an optional solvent, which is water or an aqueous solvent.

In a particularly preferred embodiment, the in vitro biosynthesis system provided by the present invention comprises: a eukaryotic cell extract, 4-hydroxyethyl piperazine ethanesulfonic acid, potassium acetate, magnesium acetate, adenosine triphosphate (ATP), guanosine triphosphate (GTP), cytidine triphosphate (CTP), uridine triphosphate (UTP), amino acid mixture, phosphocreatine, dithiothreitol (DTT), creatine phosphokinase, RNase inhibitor, luciferin, DNA of luciferase and RNA polymerase.

In the present invention, the RNA polymerase is not particularly limited, and can be one or more RNA polymerases. A typical RNA polymerase is T7 RNA polymerase.

In the present invention, the proportion of the eukaryotic cell extract in the in vitro biosynthesis system is not particularly limited; usually the eukaryotic cell extract in the in vitro biosynthesis system accounts for 20-70%, preferably 30-60%, and more preferably 40-50%, by volume.

In the present invention, the eukaryotic cell extract does not contain intact cells. Typical eukaryotic cell extract comprises various types of RNA polymerases for RNA synthesis, and factors for protein translation including ribosomes, transfer RNA (tRNA), aminoacyl-tRNA synthetase as well as factors required for protein synthesis including initiation factors, elongation factors and termination release factors. In addition, the eukaryotic cell extract also comprises some other proteins derived from the cytoplasm of eukaryotic cells, especially soluble proteins.

In the present invention, the protein content of the eukaryotic cell extract is 20-100 mg/mL, preferably 50-100 mg/mL. The method for measuring the protein content is Coomassie brilliant blue assay.

In the present invention, the preparation method for the eukaryotic cell extract is not limited. A preferred preparation method comprises the following steps:
 (i) providing eukaryotic cells;
 (ii) washing the eukaryotic cells to obtain washed eukaryotic cells;
 (iii) treating the washed eukaryotic cells with a cell lysis treatment to obtain a crude eukaryotic cell extract; and
 (iv) treating the crude eukaryotic extract via solid-liquid separation to obtain the liquid phase (i.e., the eukaryotic cell extract).

In the present invention, the method of solid-liquid separation is not particularly limited. A preferred method is centrifugation.

In a preferred embodiment, the centrifugation is carried out in a liquid state.

In the present invention, the centrifugation condition is not particularly limited. A preferred centrifugation condition is in the range of 5000 g-100000 g, preferably in the range of 8000 g-30000 g.

In the present invention, the centrifugation time is not particularly limited. A preferred centrifugation time is in the range of 0.5 minutes to 2 hours, preferably in the range of 20 minutes to 50 minutes.

In the present invention, the temperature of the centrifugation is not particularly limited. Preferably, the centrifugation is carried out at 1-10° C., preferably at 2-6° C.

In the present invention, the washing treatment method is not particularly limited. A preferred washing treatment method is to carry out the treatment using a washing solution of pH 7-8 (preferably, pH 7.4). The washing solution is not particularly limited. A typical washing solution is selected from the group consisting of potassium 4-hydroxyethylpiperazine ethanesulfonate, potassium acetate, magnesium acetate, and combinations thereof.

In the present invention, the method for cell lysis treatment is not particularly limited. A preferred method for cell lysis treatment includes high-pressure lysis and freeze-thaw (e.g., treatment at liquid-nitrogen low temperature) lysis.

The mixture of nucleoside triphosphates in the in vitro biosynthesis system comprises adenosine triphosphate, guanosine triphosphate, cytidine triphosphate and uridine triphosphate. In the present invention, the concentration of various single nucleotides are not particularly limited. The concentration of each single nucleotide is usually in the range of 0.5-5 mM, preferably in the range of 1.0-2.0 mM.

The amino acid mixture in the in vitro biosynthesis system may include natural or unnatural amino acids, and may include amino acids of D-type or L-type. Representative amino acids include, but are not limited to, 20 types of natural amino acids: glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine and histidine. The concentration of each type of amino acid is usually in the range of 0.01-0.5 mM, preferably in the range of 0.02-0.2 mM, such as 0.05 mM, 0.06 mM, 0.07 mM and 0.08 mM.

In a preferred embodiment, the in vitro biosynthesis system further comprises polyethylene glycol (PEG) or the like. The concentration of PEG or the like is not particularly limited. Generally, based on the total weight of the biosynthesis system, the concentration (w/v) of PEG or the like is in the range of 0.1-8%, preferably in the range of 0.5-4%, and more preferably in the range of 1-2%. Representative embodiments of PEG include, but are not limited to, PEG3000, PEG8000, PEG6000 and PEG3350. It should be understood that the system of the present invention may also include polyethylene glycols of other various molecular weights (such as PEG 200, 400, 1500, 2000, 4000, 6000, 8000, 10000, etc.).

In a preferred embodiment, the in vitro biosynthesis system further comprises sucrose. The concentration of sucrose is not particularly limited. Generally, based on the total weight of the protein synthesis system, the concentration of sucrose is in the range of 0.03-40 wt %, preferably in the range of 0.08-10 wt %, and more preferably in the range of 0.1-5 wt %.

A particularly preferred in vitro biosynthesis system comprises, in addition to the eukaryotic cell extract, the following components: 22 mM 4-hydroxyethyl piperazine ethanesulfonic acid of pH 7.4, 30-150 mM potassium acetate, 1.0-5.0 mM magnesium acetate, 1.5-4 mM nucleoside triphosphate mixture, 0.08-0.24 mM amino acid mixture, 25 mM phosphocreatine, 1.7 mM dithiothreitol, 0.27 mg/mL creatine phosphokinase, 1%-4% PEG, 0.5%-2% sucrose, 8-20 ng/μL DNA of firefly luciferase and 0.027-0.054 mg/mL T7 RNA polymerase.

Ω Sequence

As used herein, the term "Ω sequence" (i.e., omega sequence) refers to the 5' leading sequence (5' leader sequence) of the tobacco mosaic virus genome, and it is a translation enhancer of the virus. The DNA sequence of Ω contains 68 base pairs, comprising direct repeat modules of 8-basepair (ACAATTAC) in quantities of 1-6 (preferably 2-4, more preferably 3) and $(CAA)_p$ modules in quantities of 1-5 (preferably 1-3, more preferably 1), wherein p is in the range of 6-12, preferably in the range of 8-10. These two modules are key to the translation-enhancing function of the Ω sequence. In the yeast-based in vitro protein synthesis system of the present invention, the Ω sequence can initiate a cap-independent protein translation, which may be achieved by recruiting the translation initiation factor eIF4G. However, the efficiency of the protein translation initiated by the Ω sequence is relatively low. The structural sequence of the Ω sequence needs to be optimized, and needs to cooperate with other DNA elements or proteins to enhance the efficiency of protein translation.

Kozak Sequence

Analyzing the upstream and downstream sequences of the translation initiation codon (AUG) in the mRNA molecules of known eukaryotes helps to find a consensus sequence which is called "Kozak sequence". The Kozak sequence has been verified to enhance the translation initiation efficiency of mRNA. The Kozak sequence of different species are often different. For example, the Kozak sequence of *Saccharomyces cerevisiae* and the Kozak sequence of mammalian cells are significantly different.

The Kozak sequence used in the present invention comprises 6-12 (preferably, 8-10) oligomeric chains of adenine deoxynucleoside, a translation initiation codon (such as ATG, ATA, ATT, GTG, TTG, etc., preferably ATG) and a serine codon (such as TCT, TCC, TCA, TCG, AGT, AGC, etc., preferably TCT), and is derived from *Kluyveromyces* (preferably from *Kluyveromyces lactis*).

Exogenous Coding Sequence (Exogenous DNA)

As used herein, the terms "exogenous coding sequence" and "exogenous DNA" are used interchangeably, and both refer to an Do exogenous DNA molecule used to guide RNA or protein synthesis. Generally, the DNA molecule is linear or circular. The DNA molecule contains a sequence encoding exogenous RNA or an exogenous protein.

In the present invention, examples of the exogenous coding sequence include, but are not limited to: a genomic sequence and a cDNA sequence. The sequence encoding the exogenous protein also comprises a promoter sequence, a 5' untranslated sequence, a 3' untranslated sequence, or a combination thereof.

In the present invention, the selection of the exogenous DNA is not particularly limited. Generally, the exogenous DNA is selected from the group consisting of small non-coding RNA (sncRNA), long non-coding RNA (lncRNA), transfer RNA (tRNA), ribozymes including glucosamine-6-phosphate synthase (glmS), small nuclear RNA (snRNA), complexes (such as spliceosome) of RNA and protein, other various non-coding RNAs, and combinations thereof.

The exogenous DNA can also be selected from the group consisting of exogenous DNAs encoding luciferin, luciferases (such as firefly luciferase), green fluorescent protein, yellow fluorescent protein, aminoacyl-tRNA synthetase, glyceraldehyde-3-phosphate dehydrogenase, catalase, actin and variable regions of antibodies, DNAs of luciferase mutants, and combinations thereof.

The exogenous DNA can also be selected from the group consisting of exogenous DNAs encoding α-amylase, enterocin A, hepatitis C virus E2 glycoprotein, insulin precursors, interferon αA, interleukin-1β, lysozyme, serum albumins, single-chain variable fragment (scFv) of antibodies, transthyretin, tyrosinase, xylanase, and combinations thereof.

In a preferred embodiment, the exogenous DNA encodes a protein selected from the group consisting of green fluorescent protein (enhanced GFP, eGFP), yellow fluorescent protein (YFP), *E. coli* β-galactosidase (LacZ), human lysine-tRNA synthetase, human leucine-tRNA synthetase, *Arabidopsis thaliana* glyceraldehyde-3-phosphate dehydrogenase, murine catalase, and combinations thereof Nucleic Acid Construct The present invention provides a nucleic acid construct, comprising a nucleic acid sequence of Formula I:

$$Z1\text{-}Z2\text{-}Z3\text{-}Z4\text{-}Z5 \quad (I)$$

wherein,

Z1~Z5 are respectively an element as part of the construct;

each "-" is independently a bond or a nucleotide linking sequence;

Z1 is an enhancer element, and the enhancer element comprises an IRES element;

Z2 is a 5' leading sequence of tobacco mosaic virus, that is Ω sequence;

Z3 is an oligomeric chain $[oligo(A)]_n$ of adenine deoxynucleotide;

Z4 is a translation initiation codon;

Z5 is a serine codon;

Wherein, Z3, Z4 and Z5 constitute a Kozak sequence, and the Kozak sequence is derived from yeast.

The present invention also provides a nucleic acid construct comprising a structure of formula II from 5' to 3':

$$Z1\text{-}Z2\text{-}Z3\text{-}Z4\text{-}Z5\text{-}Z6 \quad (II)$$

wherein,

Z1~Z6 are respectively an element as part of the construct;

each "-" is independently a bond or a nucleotide linking sequence;

Z1 is an enhancer element, and the enhancer element comprises an IRES element;

Z2 is a 5' leading sequence of tobacco mosaic virus, that is the Ω sequence;

Z3 is an oligomeric chain $[oligo(A)]_n$ of adenine deoxynucleotide;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

The present invention also provides a nucleic acid construct comprising a structure of Formula III from 5' to 3':

$$Z0\text{-}Z1\text{-}Z2\text{-}Z3\text{-}Z4\text{-}Z5\text{-}Z6 \quad (III)$$

wherein,

Z0~Z6 are respectively an element as part of the construct;

each "-" is independently a bond or a nucleotide linking sequence;

Z0 is a promoter element, and the promoter element is selected from the group consisting of T7 promoter, T3 promoter, SP6 promoter, and combinations thereof;

Z1 is an enhancer element, and the enhancer element comprises an IRES element;

Z2 is a 5' leading sequence of tobacco mosaic virus, that is the Ω sequence;

Z3 is an oligomeric chain [oligo(A)]$_n$ of adenine deoxynucleotide;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

The present invention also provides a nucleic acid construct comprising a structure of Formula IV from 5' to 3':

$$Z0'-Z1-Z2-Z3-Z4-Z5-Z6 \quad (IV)$$

wherein,

Z0'~Z6 are respectively an element as part of the construct;

each "-" is independently a bond or a nucleotide linking sequence;

Z0' is GAA;

Z1 is an enhancer element, and the enhancer element comprises an IRES element;

Z2 is a 5' leading sequence of tobacco mosaic virus, that is the Ω sequence;

Z3 is an oligomeric chain [oligo(A)]$_n$ of adenine deoxynucleotide;

Z4 is a translation initiation codon;

Z5 is a serine codon;

Z6 is a coding sequence of an exogenous protein;

Wherein, Z3, Z4 and Z5 constitute a Kozak sequence, and the Kozak sequence is derived from yeast.

In the present invention, the selection of the coding sequence of the exogenous protein is not particularly limited. Generally, the coding sequence of the exogenous protein is selected from the group consisting of exogenous DNAs encoding luciferin, luciferases (e.g., firefly luciferase), green fluorescent protein, yellow fluorescent protein, aminoacyl-tRNA synthetase, glyceraldehyde-3-phosphate dehydrogenase, catalase, actin and variable regions of antibodies, DNAs of luciferase mutants, and combinations thereof.

The coding sequence of the exogenous protein can also encode a protein selected from the group consisting of α-amylase, enterocin A, hepatitis C virus E2 glycoprotein, insulin precursors, interferon αA, interleukin-1β, lysozyme, serum albumins, single-chain variable fragment (scFv) of antibodies, transthyretin, tyrosinase, xylanase, and combinations thereof.

In addition, the nucleic acid construct of the present invention can be linear or circular. The nucleic acid construct of the present invention can be single-stranded or double-stranded. The nucleic acid construct of the present invention can be DNA, RNA, or DNA/RNA hybrid.

In a preferred embodiment, the sequence of the nucleic acid construct of the present invention is any one of SEQ ID NO.: 2-17.

In a preferred embodiment, the sequence of the nucleic acid construct is any one of SEQ ID NO.: 2-9.

In a preferred embodiment, the sequence of the nucleic acid construct is SEQ ID NO.: 3, 4 or 6.

In a preferred embodiment, the sequence of the nucleic acid construct of the present invention is any one of SEQ ID NO.: 85-87

In another preferred embodiment, the construct further comprises elements or combinations selected from the group consisting of promoters, terminators, poly (A) elements, transport elements, gene targeting elements, selection marker genes, enhancers, resistance genes, and transposase-encoding genes.

Various selectable marker genes can be used in the present invention, including but not limited to: auxotrophic markers, resistance markers, and reporter gene markers. The application of selectable markers plays a role in the screening of recombinant cells (recons), where the receptor cells can be significantly distinguished from untransformed cells. The auxotrophic marker can be complementary to the mutant gene of the receptor cell with the help of transferred marker gene, so that the receptor cell exhibits wild-type growth. The resistance marker refers to that the resistance gene is transferred into the receptor cell, and the transferred gene allow the receptor cell to exhibit drug resistance at a certain drug concentration. As a preferred mode of the present invention, resistance markers are used to achieve convenient screening of recombinant cells.

In the present invention, the application of the nucleic acid construct of the present invention in the yeast-based in vitro biosynthesis system of the present invention (such as a yeast-based protein biosynthesis system) can significantly improve the efficiency of exogenous protein translation. Specifically, the relative light unit value for indicating the activity of luciferase synthesized by using the nucleic acid construct of the present invention is very high, wherein the relative light unit value when using the nucleic acid construct of the present invention (such as KlNCE102-Ω-10A) was 1.65 times that when using the Ω-10A sequence.

Vector, Genetically Engineered Cell

The invention also provides a vector or a vector combination comprising the nucleic acid construct of the present invention. Preferably, the vector is selected from the group consisting of bacterial plasmids, phages (i.e., bacteriophages), yeast plasmids, animal cell vectors, and shuttle vectors; the vector is a transposon vector. Methods for preparing recombinant vectors are well known to those of ordinary skill in the art. Any plasmid or vector can be used as long as it can be replicated and stable in the host.

Those of ordinary skill in the art can construct an expression vector containing the promoter and/or the objective gene sequence of the present invention using well-known methods. These methods include in vitro recombinant DNA technology, DNA synthesis technology, in vivo recombinant technology and so on.

The present invention also provides a genetically engineered cell. The genetically engineered cell comprises the construct, the vector or the vector combination; or the chromosome of the genetically engineered cell is integrated with the construct or the vector. In another preferred embodiment, the genetically engineered cell further comprises a vector containing a transposase-encoding gene, or the chromosome of the genetically engineered cell is integrated with a transposase gene.

Preferably, the genetically engineered cell is a eukaryotic cell.

In another preferred embodiment, the eukaryotic cell includes, but is not limited to: human cell, Chinese hamster ovary cell, insect cell, wheat germ cell, rabbit reticulocyte and other higher eukaryotic cells.

In another preferred embodiment, the eukaryotic cell includes, but is not limited to: yeast cell (preferably, *Kluyveromyces* cell, more preferably *Kluyveromyces lactis* cell).

The construct or vector of the present invention can be used to transform appropriate genetically engineered cell. The genetically engineered cell can be a prokaryotic cell, such as *E. coli, streptomyces, Agrobacterium*; or be a lower eukaryotic cell, such as yeast cell; or be a higher animal cell, such as insect cell. Those of ordinary skill in the art know how to select appropriate vector and genetically engineered cell. Transformation of genetically engineered cell with recombinant DNA can be carried out using conventional techniques well known to those skilled in the art. When the host is a prokaryote (such as *E. coli*), it can be treated using a $CaCl_2$ method or an electroporation method. When the host is a eukaryote, the following DNA transfection methods can be selectively used: calcium phosphate coprecipitation method and conventional mechanical methods (such as microinjection, electroporation, liposome packaging, etc.). Transformation of plant cell can be performed also by using a method such as *Agrobacterium*-mediated transformation or gene gun transformation, for example, leaf disc method, immature embryo transformation method, flower bud soaking method, and the like.

In Vitro High-Throughput Protein Synthesis Method

The present invention provides an in vitro high-throughput protein synthesis method, comprising the following steps:
(i) in the presence of a eukaryote-based in vitro biosynthesis system, providing the nucleic acid construct selected from the first to fourth aspects of the present invention; and
(ii) under suitable conditions, incubating the eukaryote-based in vitro biosynthesis system of step (i) for a period of time T1 to synthesize the exogenous protein.

In another preferred embodiment, the method further comprises:
(iii) optionally isolating or detecting the exogenous protein from the eukaryote-based in vitro biosynthesis system.

The main advantages of the present invention include:
(1) For the first time, the present invention found that a nucleic acid construct comprising a promoter, a yeast-derived IRES, the Ω sequence, a Kozak sequence and the coding sequence of an exogenous protein, when being used in the eukaryote-based in vitro biosynthesis system of the present invention (such as a yeast-based in vitro protein synthesis system), can significantly improve the efficiency of exogenous protein translation.

(2) The endogenous IRESs of eukaryotic cells of the present invention concatenated in tandem with the Ω sequence and a Kozak sequence can enhance the efficiency of protein translation initiation in the eukaryote-based in vitro biosynthesis system. In the aspect of enhancing the efficiency of translation initiation, the tandem DNA elements are advantageous over the tandem sequence (Ω-10A) concatenating only the latter two. Wherein, in the *Kluyveromyces lactis* based in vitro biosynthesis system, the relative light unit (RLU) value of firefly luciferase (Fluc) when using KlNCE102-Ω-10A to initiate synthesis reached $1.67 \times 10^9$, which was 1.65-folds of that when using the Ω-10A sequence.

(3) Compared with *Saccharomyces cerevisiae*, *Kluyveromyces lactis* can be used for the protein production in the food and pharmaceutical fields due to its safety and high efficiency, as well the advantages of in vitro biosynthesis system (such as suitability for high-throughput protein synthesis and screening, capability of synthesizing toxic proteins, short time, low cost, etc.), so the in vitro biosynthesis system derived from *Kluyveromyces lactis* cells can also be widely used in the related fields of protein synthesis.

(4) The nucleic acid construct provided by the present invention not only enhances the efficiency of initiating protein translation of the eukaryote-based in vitro biosynthesis system, but more importantly, increases the possibility of *Kluyveromyces lactis* based in vitro biosynthesis systems for the synthesis of different proteins.

(5) The nucleic acid construct of the present invention not only enhances the efficiency of protein translation initiation, but also provides new concepts and new methods for designing DNA elements used for eukaryote-based cell in vitro biosynthesis systems, which can greatly raise the application of related systems in the fields of scientific research and industrial production.

(6) The present invention found for the first time that combining a strong promoter (e.g., T7 promoter, T3 promoter, SP6 promoter) with the nucleic acid construct of the present invention can also achieve very high protein synthesis efficiency.

(7) The present invention found for the first time that placing three residues of GAA upstream of the nucleic acid construct of the present invention can also achieve very high protein synthesis efficiency.

The present invention is further described below in conjunction with specific examples. It should be understood that these examples are only used to illustrate the present invention and not to limit the scope of the present invention. With respect to the experimental methods without specifically described conditions in the following examples, one person may generally follow conventional conditions, such as the conditions described in Sambrook et al., Molecular Cloning: A Laboratory Manual (New York: Cold Spring Harbor Laboratory Press, 1989), or follow the conditions recommended by the manufacturer. Unless otherwise stated, percentages and portions refer to percentages and portions by weight.

Unless otherwise specified, materials and reagents used in the examples of the present invention are all commercially available products.

Figure 1:
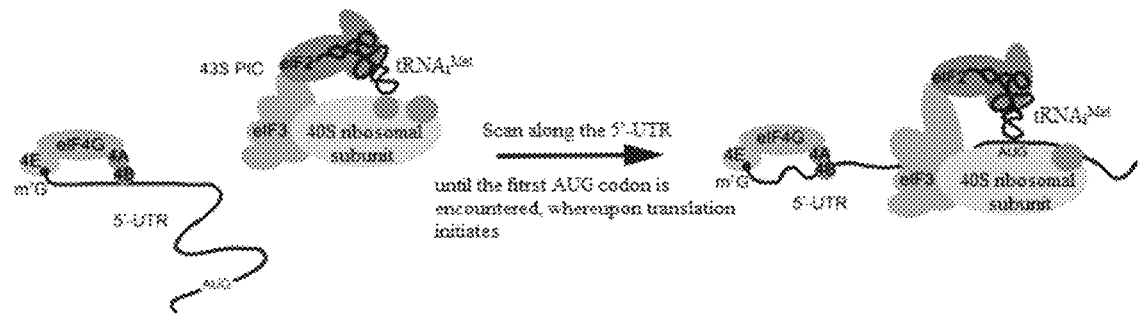
FIG. 1 shows the key role of the 5'-UTR sequence in protein translation initiation in biosynthesis. The 5'-UTR mainly plays a role in regulating protein translation initiation and in stabilizing mRNA in cells. (A) In the process of the cap-dependent protein translation initiation, the 5'-UTR plays an important role in recruiting translation initiation factors and 43S pre-initiation complex (PIC), and it can also regulate the scanning of 43S PIC and translation initiation. In the process of the cap-independent protein translation initiation, both (B) 5'-UTR with secondary structures and (C) 5'-UTR without secondary structures need the help of some protein factors and are very important for recruiting 43S PIC.
Figure 1:
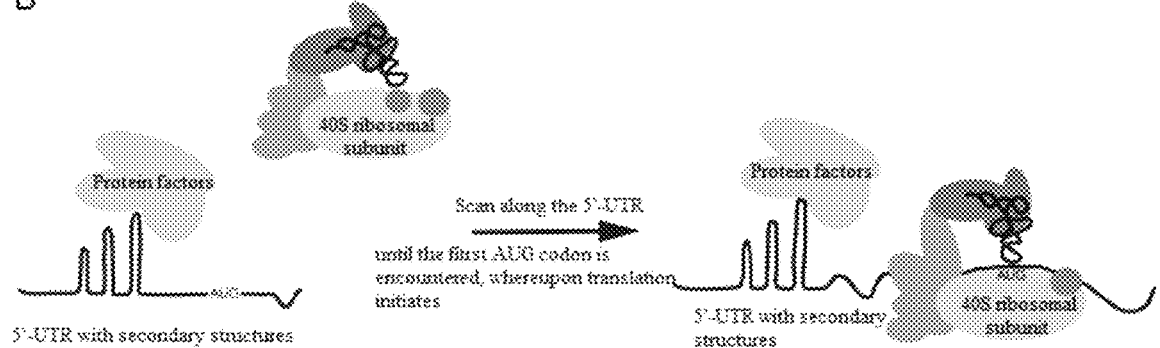
Figure 1:
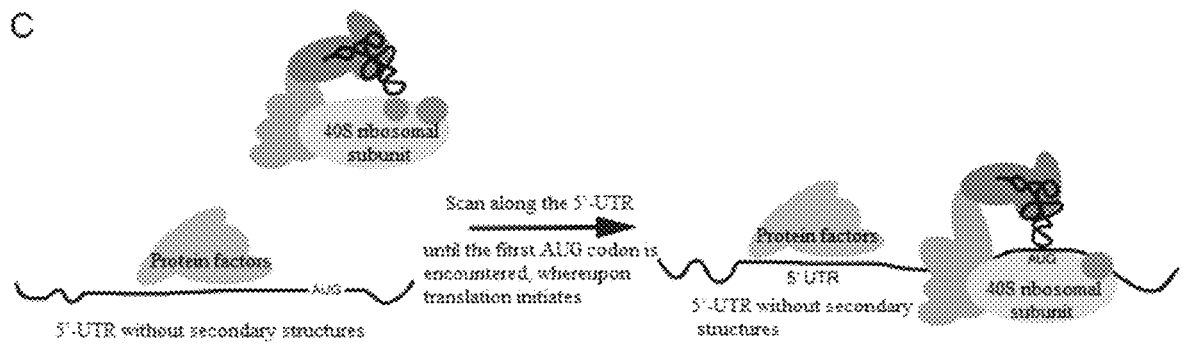
Figure 2:
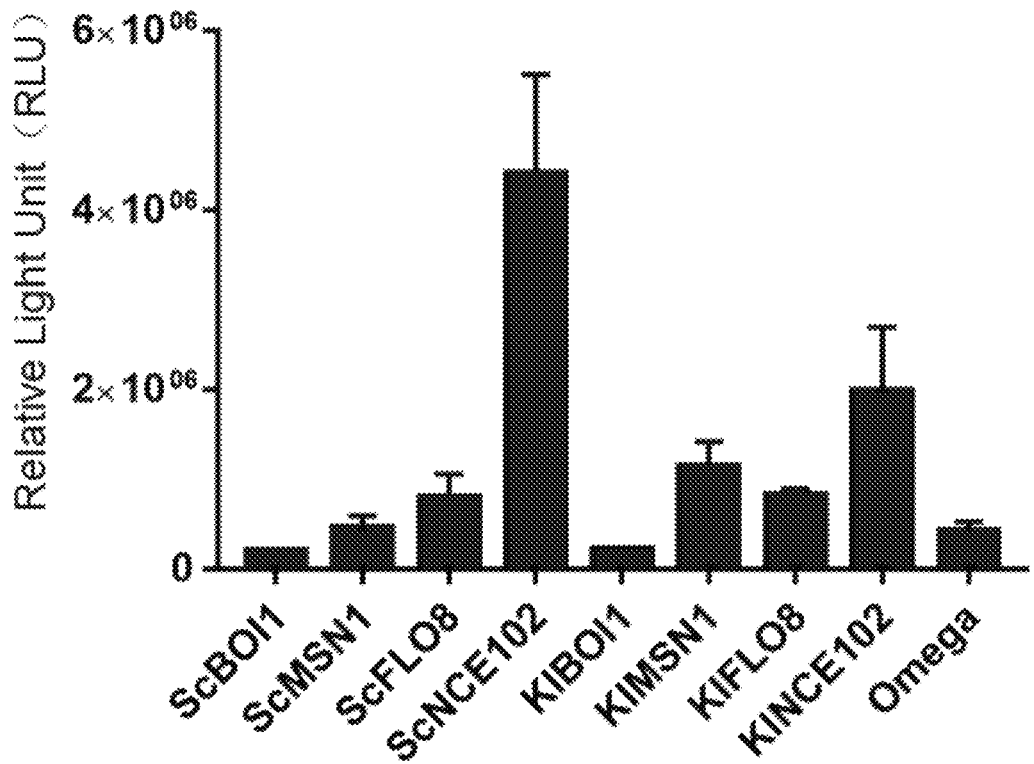
FIG. 2 shows the efficiency of initiating protein synthesis of eukaryotic endogenous IRESs in an in vitro protein synthesis system. Eight homologous IRESs selected from IRESs derived from *Saccharomyces cerevisiae* and *Kluyveromyces lactis* were used in a yeast-based in vitro protein synthesis system. Compared with the traditional Ω sequence, the relative light unit (RLU) value of luciferase when using six IRESs (ScFLO8, ScMSN1, ScNCE102, KlFLO8, KlMSN1 and KlNCE102) to initiate its synthesis exceeded that when using the Ω sequence.

Example 1: Design of DNA Elements Concatenating an Endogenous IRES of a Eukaryotic Cell, the Ω Sequence and a *Kluyveromyces lactis*-Specific Kozak Sequence in Tandem 1.1 Determination of endogenous IRESs in *Kluyveromyces lactis* and *Saccharomyces cerevisiae*: 4 endogenous IRESs of *Kluyveromyces lactis* and the IRESs corresponding to their homologous proteins in *Saccharomyces cerevisiae* (as shown in Table 1) are capable of initiating in vitro protein synthesis. Among the IRESs to initiate the synthesis of Fluc, six IRESs (KlFLO8, KlMSN1, KlNCE102, ScFLO8, ScMSN1 and ScNCE102) showed a higher relative light unit (RLU) value than the traditional Ω sequence, and the other two (KlBOI1 and ScBOI1) showed a lower RLU value than the Ω Sequence (as shown in FIG. 2). These 8 IRESs were determined to be concatenated in tandem with the Ω sequence and a Kozak sequence.

1.2 Determination of 16 tandem elements: concatenate in tandem the 8 endogenous IRESs with the Ω sequence and a *Kluyveromyces lactis*-specific Kozak sequence, and vary the upstream or downstream location of the IRES relative to the Ω sequence; consequently 16 tandem DNA elements in total were designed (KlFLO8, KlMSN1, KlNCE102, KlBOI1, ScFLO8, ScMSN1, ScNCE102 and ScBOI1-Ω-10A as well as Ω-KlFLO8, KlMSN1, KlNCE102, KlBOI1, ScFLO8, ScMSN1, ScNCE102 and ScBOI1-10A). The sequences of the tandem elements shown in SEQ ID NO.: 2-17 correspond to the sequences of the above tandem DNA elements (KlFLO8, KlMSN1, KlNCE102, KlBOI1, ScFLO8, ScMSN1, ScNCE102 and ScBOI1-Ω-10A as well as Ω-KlFLO8, KlMSN1, KlNCE102, KlBOI1, ScFLO8, ScMSN1, ScNCE102 and ScBOI1-10A) respectively in sequence.

1.3 Design of tandem elements with a reporter protein gene (Fluc): the 16 tandem elements as designed above were inserted into an existing Ω-10A-Fluc plasmid (obtained from KangMa-Healthcode (Shanghai) Biotech Co., Ltd, and the Ω-10A sequence is shown in SEQ ID NO.:1) to replace Ω-10A and 16 new plasmids were formed; the resultant 16 new plasmids were respectively KlFLO8-Ω-10A-Fluc, KlMSN1-Ω-10A-Fluc, KlNCE102-Ω-10A-Fluc, KlBOI1-Ω-10A-Fluc, ScFLO8-Ω-10A-Fluc, ScMSN1-Ω-10A-Fluc, ScNCE102-Ω-10A-Fluc, ScBOI1-Ω-10A-Fluc, Ω-KlFLO8-10A-Fluc, Ω-KlMSN1-10A-Fluc, Ω-KlNCE102-10A-Fluc, Ω-KlBOI1-10A-Fluc, Ω-ScFLO8-10A-Fluc, Ω-ScMSN1-10A-Fluc, Ω-ScNCE102-10A-Fluc and Ω-ScBOI1-10A-Fluc. Among them, the sequences of KlNCE102-Ω-10A-Fluc, ScFLO8-Ω-10A-Fluc and KlMSN1-Ω-10A-Fluc are respectively shown in SEQ ID NO.: 85-87.

TABLE 1

Related Genes in *Saccharomyces cerevisiae* and *Kluyveromyces lactis*

| Gene Name | Open Reading Frames (ORFs) |
| --- | --- |
| ScBOI1 | YBL085w |
| ScFLO8 | YER109c |
| ScNCE102 | YPR149w |
| ScMSN1 | YOL116w |
| KlBOI1 | KLLA0E20879g |
| KlFLO8 | KLLA0E20725g |
| KlNCE102 | KLLA0D16280g |
| KlMSN1 | KLLA0A07337g |

Example 2: Construction of Plasmids Containing the Tandem DNA Element for the In Vitro Protein Synthesis System 2.1 Construction of plasmids: insert 8 endogenous IRESs respectively into the Ω-10A-Fluc plasmid, which are respectively located upstream or downstream of the Ω sequence. The specifically used primers are shown in Table 2.

The specific construction process for one plasmid is as follow:

The IRES fragment to be inserted and the Ω-10A-Fluc vector plasmid were respectively amplified by PCR by using two pairs of primers, and 10 μL of each PCR amplification product were taken and mixed together. Then, 1 μL DpnI was added into the 20 μL mixture of the amplification products followed by incubation at 37° C. for 6 hours. Thereafter, 4 μL of the DpnI-treated product was added into 50 μL of DH5a competent cells. The mixture was placed on ice for 30 minutes and heat-shocked at 42° C. for 45 seconds. Subsequently, the mixture was placed on ice for 3 minutes, added with 200 μL of LB liquid medium, and then cultured with shaking at 37° C. for 4 h. Thereafter, the mixture was coated on an LB solid medium containing Amp antibiotic and cultured overnight. Six monoclonal colonies were picked out for carrying out proliferation culture. After being confirmed the correctness by sequencing, the plasmid was extracted and stored.

TABLE 2

Primers for PCR Amplification

| Plasmid Name | Primer Name of Vector Amplification | SEQ ID NO.: | Primer Name of IRES Amplification | SEQ ID NO.: |
| --- | --- | --- | --- | --- |
| KlFLO8-Ω-10A-Fluc | PF_FLO8KL_Omega | 18 | PF_T7pro_FLO8KL | 20 |
|  | PR_FLO8KL_T7pro | 19 | PR_Omega_FLO8KL | 21 |
| KlMSN1-Ω-10A-Fluc | PF_MSN1KL_Omega | 22 | PF_T7pro_MSN1KL | 24 |
|  | PR_MSN1KL_T7pro | 23 | PR_Omega_MSN1KL | 25 |
| KlNCE102-Ω-10A-Fluc | PF_KLNCE102_Omega | 26 | PF_T7pro_KLNCE102 | 28 |
|  | PR_KLNCE102_T7pro | 27 | PR_Omega_KLNCE102 | 29 |
| KlBOI1-Ω-10A-Fluc | PF_BOI1KL_Omega | 30 | PF_T7pro_BOI1KL | 32 |
|  | PR_BOI1KL_T7pro | 31 | PR_Omega_BOI1KL | 33 |
| ScFLO8-Ω-10A-Fluc | PF_FLO8_Omega | 34 | PF_T7pro_FLO8 | 36 |
|  | PR_FLO8_T7pro | 35 | PR_Omega_FLO8 | 37 |
| ScMSN1-Ω-10A-Fluc | PF_MSN1_Omega | 38 | PF_T7pro_MSN1 | 40 |
|  | PR_MSN1_T7pro | 39 | PR_Omega_MSN1 | 41 |
| ScNCE102-Ω-10A-Fluc | PF_NCE102_Omega | 42 | PF_T7pro_NCE102 | 44 |
|  | PR_NCE102_T7pro | 43 | PR_Omega_NCE102 | 45 |
| ScBOI1-Ω-10A-Fluc | PF_BOI1_Omega | 46 | PF_T7pro_BOI1 | 48 |
|  | PR_BOI1_T7pro | 47 | PR_Omega_BOI1 | 49 |
| Ω-KlFLO8-10A-Fluc | O-Flo8(KL)_PF-2 | 50 | Flo8(KL)_F | 52 |
|  | O-Flo8(KL)-PR-2 | 51 | Flo8(KL)_R | 53 |
| Ω-KlMSN1-10A-Fluc | PF_pET21a_KLMSN1_10A | 54 | PF_KLMSN1_Omega_pET21a | 56 |
|  | PR_pET21a_KLMSN1_Omega | 55 | PR_KLMSN1_10A_pET21a | 57 |
| Ω-KlNCE102-10A-Fluc | O-IRES-PF | 58 | NCE102(KL)-F | 60 |
|  | O-IRES-PR | 59 | NCE102(KL)-R | 61 |
| Ω-KlBOI1-10A-Fluc | PF_pET21a_10A_KLBOI | 62 | PF_KLBOI_Omega_pET21a | 64 |
|  | PR_pET21a_Omega_KLBOI | 63 | PR_KLBOI_10A_pET21a | 65 |
| Ω-ScFLO8-10A-Fluc | O-FLO8-PF-2 | 66 | Flo8_F | 68 |
|  | O-FLO8-PR-2 | 67 | Flo8_R | 69 |
| Ω-ScMSN1-10A-Fluc | PF_pET21a_MSN1_10A | 70 | PF_MSN1_Omega_pET21a | 72 |
|  | PR_pET21a_MSN1_Omega | 71 | PR_MSN1_10A_pET21a | 73 |

TABLE 2-continued

Primers for PCR Amplification

| Plasmid Name | Primer Name of Vector Amplification | SEQ ID NO.: | Primer Name of IRES Amplification | SEQ ID NO.: |
|---|---|---|---|---|
| Ω-ScNCE102-10A-Fluc | O-IRES-PF2<br>O-IRES-PR2 | 74<br>75 | NCE102-F<br>NCE102-R | 76<br>77 |
| Ω-ScBOI1-10A-Fluc | PF_pET21a_10A_BOI1<br>PR_pET21a_Omega_BOI1 | 78<br>79 | PFBOI1_Omega_pET21a<br>PR_BOI1_10A_pET21a | 80<br>81 |

Example 3: Application of Tandem DNA Elements in the Yeast-Based In Vitro Protein Synthesis System 3.1 The fragment containing the tandem DNA element and Fluc in all plasmids, which are between the T7 transcription initiation sequence and the termination sequence, were amplified by the PCR method while using T7_pET21a_F:CGCGAAATTAATACGACTCACTATAGG (SEQ ID NO.: 82) and T7ter_pET21a_R: TCCGGATATAGTTCCTCCTTTCAG (SEQ ID NO.: 83) as primers.

The amplified DNA fragments were purified and enriched using the ethanol precipitation method: 1/10 volume of 3 M sodium acetate (pH 5.2) was added to the PCR product, and then 95% ethanol of 2.5-3 folds by volume was added (relative to the volume after the addition of sodium acetate), followed by incubation on ice for 15 minutes. Thereafter, the mixture was centrifuged at a speed higher than 14000 g for 30 minutes at room temperature, and the supernatant was removed. The precipitate was washed with 70% ethanol, and then centrifuged for 15 minutes followed by removal of the supernatant. The precipitate was dissolved with ultrapure water to measure the DNA concentration.

3.2 According to the instructions for use, the purified DNA fragments were added to the self-made *Kluyveromyces lactis* based in vitro protein synthesis system. The abovesaid reaction system was placed in an environment of 25-30° C., and let the mixture stand for incubation for about 2-6 hours. After completion, an equal volume of luciferin as the substrate for Fluc was added into the wells for above reactions of a 96-well or 384-well white plate, which was immediately placed in an Envision 2120 multifunctional microplate reader (Perkin Elmer), and the absorbance was read to detect the activity of Fluc, where the unit of activity is relative light unit (RLU) value, as shown in FIG. 2.

3.3 The DNA fragment (Ω-10A-Fluc) group without endogenous IRES sequences of eukaryotic cells was used as a control, and a reaction group with no addition of DNA template was used as a negative control (NC). Three independent samples were used for each group.

Experimental Results

1. Design of DNA Elements Concatenating an Endogenous IRES of a Eukaryotic Cell and the Ω Sequence with a *Kluyveromyces lactis*-Specific Kozak Sequence in Tandem A total of 16 tandem DNA elements were designed, and all of the 16 elements were inserted respectively into the Ω-10A-Fluc plasmid to replace the Ω-10A sequence, and 16 plasmids used for the in vitro protein synthesis were formed.
2. Construction of Plasmids Containing the Tandem DNA Element for the In Vitro Protein Synthesis System After a lot of attempt, 16 plasmids in total for the in vitro protein synthesis system were successfully constructed.

Figure 3:
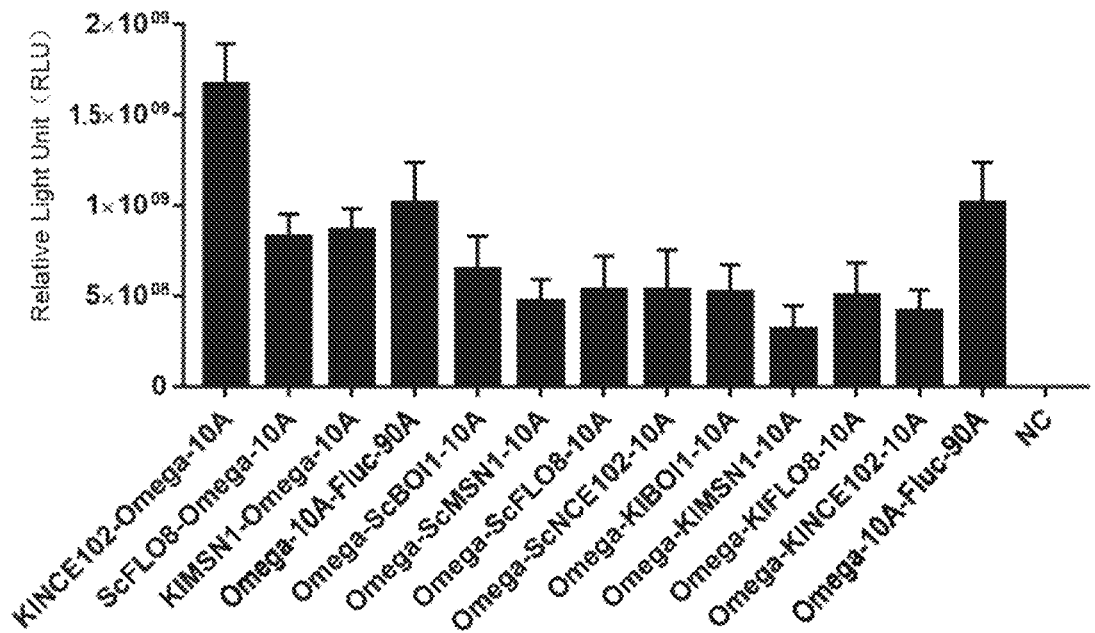
FIG. 3 shows a comparison of tandem DNA elements in the efficiency of initiating protein synthesis in an in vitro protein synthesis system. Eight IRESs respectively located either upstream or downstream of the Ω sequence, were respectively concatenated with the Ω sequence and a *Kluyveromyces lactis*-specific Kozak sequence in tandem, and sixteen tandem DNA elements were constructed. The sixteen tandem DNA elements were used in an in vitro protein synthesis system, wherein, the relative light unit (RLU) value of luciferase when using KlNCE102-Ω-10A to initiate synthesis exceeded that when using the tandem element Ω-10A concatenating the Ω sequence and a Kozak sequence, and was 1.65-folds relative to the RLU value when using Ω-10A. Secondly, the relative light unit values when using another two tandem elements, ScFLO8-Ω-10A and KlMSN1-Ω-10A, were close to the RLU value when using Ω-10A, respectively reaching 81.68% and 85.35% of the RLU value when using Ω-10A.

3. Application of Tandem DNA Elements in the Yeast-Based In Vitro Protein Synthesis System As shown in FIG. 3, among three selected tandem DNA elements, with respect to the relative light unit (RLU) value of firefly luciferase in the yeast-based in vitro protein synthesis system, only the RLU value by KlNCE102-Ω-10A exceeded that by the Ω-10A sequence; wherein, the relative light unit value by KlNCE102-Ω-10A reached $1.67 \times 10^9$, which is 1.65-folds relative to that by the Ω-10A sequence (the relative light unit value by the Ω-10A sequence was $1.01 \times 10^9$). What's more, the relative light unit values by ScFLO8-Ω-10A and KlMSN1-Ω-10A were close to that by the Ω-10A sequence, respectively reaching 81.68% and 85.35% of the RLU value by the Ω-10A sequence.

Since within the range of linear relationship between the relative light unit (RLU) value via the detecting instrument and the protein concentration, the relative light unit value by KlNCE102-Ω-10A which showed the highest activity was 1.65 times that by the Ω-10A sequence, it indicates that the tandem DNA element can enhance protein synthesis to about 1.65 folds.

Figure 4:
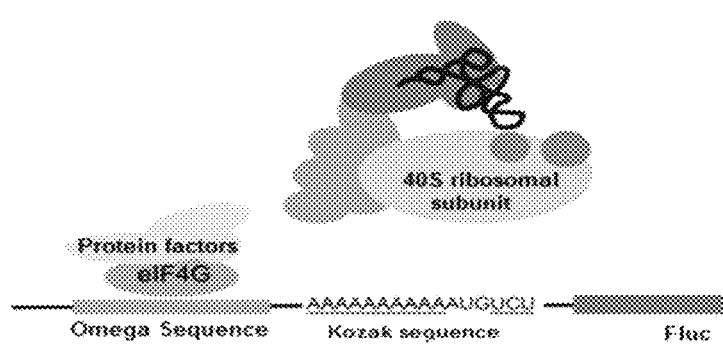
FIG. 4 shows the mechanism of enhancing the efficiency of in vitro protein translation initiation by the KlNCE102-Ω-10A sequence in the present invention. (A) The Ω sequence needs to combine the translation initiation factor eIF4G for recruiting 43S PIC and initiating protein translation. (B) KlNCE102 is an A-rich RNA sequence capable of recruiting poly (A) binding protein Pab1. Pab1 can interact with eIF4G, thereby enhancing the recruitment effect on 43S PIC and improving the efficiency of translation initiation. KlNCE102 and the Ω sequence form a synergistic effect, enhancing the translation initiation efficiency.
Figure 4:
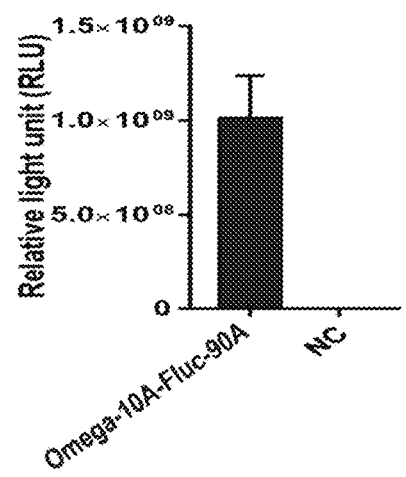
Figure 4:
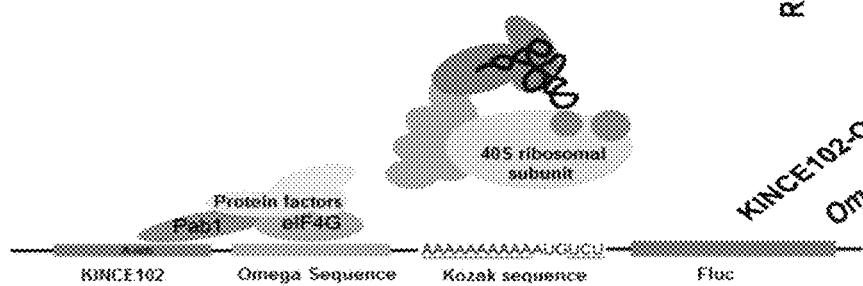
Figure 4:
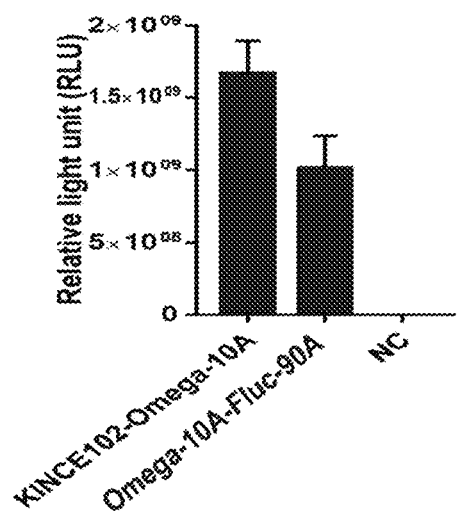

The results of the present invention indicate that: concatenating the endogenous IRES of the eukaryotic cell and the Ω sequence with a *Kluyveromyces lactis*-specific Kozak sequence in tandem can enhance the efficiency of protein synthesis; the two can recruit translation initiation factors, Pab1 and eIF4G which are capable of interacting with each other, to achieve a synergistic effect on promoting protein synthesis efficiency (as shown in FIG. 4), and can be applied to the yeast-based in vitro protein synthesis system, in which the efficiency of initiating protein synthesis can exceed the commonly used tandem element Ω-10A comprising the Ω sequence and a Kozak sequence. Wherein, the amount of the synthesized protein where the synthesis is initiated by KlNCE102-Ω-10A was 1.65 times that by the Ω-10A sequence; KlNCE102-Ω-10A raised the protein translation efficiency of the yeast-based in vitro protein synthesis system, increased the selectivity of translation elements for the *Kluyveromyces lactis* based in vitro synthesis system to initiate protein synthesis, and greatly enhanced the usability of the *Kluyveromyces lactis* based in vitro protein synthesis system.

Furthermore, according to the study results, the present invention also found that placing three residues of GAA upstream of the tandem DNA element (the 5' end of the transcribed mRNA is GAA) can also enhance protein synthesis efficiency. The relative light unit value of luciferase using the tandem of GAA and the nucleic acid construct of the present invention to mediate the in vitro synthesis was 1.28 times the RLU value when using the nucleic acid construct of the present invention alone (as shown in FIG. 5).

In addition, according to the study results, the present invention also found that the relative light unit value by the nucleic acid construct (such as KlNCE102-Ω-10A) of the present invention was 1.23 times that by KlNCE102 (as shown in FIG. 5).

All documents mentioned in the present invention are incorporated by reference in this application, just as each document is individually incorporated by reference. In addition, it should be understood that, those skilled in the art, after reading the above-taught content of the present invention, can make various changes or modifications to the present invention, and these equivalent forms also fall within the scope as defined by the appended claims of the present invention.

What is claimed is:

1. A nucleic acid construct, comprising a nucleic acid sequence of Formula I:

Z1-Z2-Z3-Z4-Z5    (I)

wherein,
Z1~Z5 are respectively an element as part of the nucleic acid construct;
each "-" is independently a bond or a nucleotide linking sequence;
Z1 is an enhancer element, comprising an IRES element, the IRES element is KINCE102;
Z2 is a 5' leading sequence of tobacco mosaic virus, that is Q sequence;
Z3 is an oligomeric chain [oligo (A)] n of adenine deoxynucleotide;
Z4 is a translation initiation codon;
Z5 is a serine codon;
wherein Z3, Z4 and Z5 constitute a Kozak sequence, and the Kozak sequence is derived from yeast.

2. The nucleic acid construct of claim 1, wherein the nucleic acid sequence of the nucleic acid construct is SEQ ID NO.: 4.

3. The nucleic acid construct of claim 1, comprising a structure of Formula II from 5' to 3':

Z1-Z2-Z3-Z4-Z5-Z6    (II)

wherein,
each "-" is independently a bond or a nucleotide linking sequence;
Z6 is a coding sequence of an exogenous protein.

4. The nucleic acid construct of claim 3, wherein Z6 is a coding sequence of an exogenous protein which is selected from the group consisting of luciferin, luciferases, green fluorescent protein, yellow fluorescent protein, aminoacyl-tRNA synthetase, glyceraldehyde-3-phosphate dehydrogenase, catalase, actin, variable regions of antibodies, luciferase mutants, a-amylase, enterocin A, hepatitis C virus E2 glycoprotein, insulin precursors, interferon αA, interleukin-1β, lysozyme, serum albumins, single-chain variable fragment of antibodies, transthyretin, tyrosinase, xylanase, and combinations thereof.

5. The nucleic acid construct of claim 3, wherein Z6 is a coding sequence of firefly luciferase.

6. The nucleic acid construct of claim 3, comprising a structure of Formula III from 5' to 3':

$$Z0\text{-}Z1\text{-}Z2\text{-}Z3\text{-}Z4\text{-}Z5\text{-}Z6 \quad (III)$$

wherein, each "-" is independently a bond or a nucleotide linking sequence;

Z0 is a promoter element selected from the group consisting of T7 promoter, T3 promoter, SP6 promoter, and combinations thereof.

7. The nucleic acid construct of claim 3, comprising a structure of Formula IV from 5' to 3':

$$Z0'\text{-}Z1\text{-}Z2\text{-}Z3\text{-}Z4\text{-}Z5\text{-}Z6 \quad (IV)$$

wherein, each "-" is independently a bond or a nucleotide linking sequence;

Z0' is GAA.

8. A vector or a vector combination, containing a nucleic acid construct as claimed in any one of claims 1 and 2-7.

9. A genetically engineered cell, wherein the genetically engineered cell has a nucleic acid construct integrated in its genome at one or more sites, or the genetically engineered cell contains a vector or a vector combination, wherein the vector or the vector combination contains the nucleic acid construct;

wherein, the nucleic acid construct is claimed in any one of claims 1 and 2-7.

10. A kit, comprising one or more reagents selected from one or more of the following Groups:

Group (a): a nucleic acid construct;

Group (b): a vector or a vector combination, wherein the vector or the vector combination contains the nucleic acid construct as defined in Group (a); and Group (c): a genetically engineered cell, wherein the genetically engineered cell has the nucleic acid construct as defined in Group (a) integrated in its genome at one or more sites, or the genetically engineered cell contains the vector or the vector combination as defined in Group (b);

wherein, the nucleic acid construct is claimed in any one of claims 1 and 2-7.

11. The nucleic acid construct of claim 2, comprising a structure of Formula III from 5' to 3':

$$Z0\text{-}Z1\text{-}Z2\text{-}Z3\text{-}Z4\text{-}Z5\text{-}Z6 \quad (III)$$

wherein, each "-" is independently a bond or a nucleotide linking sequence;

Z0 is a promoter element, the promoter element is T7 promoter;

Z6 is a coding sequence of luciferases.

* * * * *

SEQUENCE LISTING

```
<160> NUMBER OF SEQ ID NOS: 87

<210> SEQ ID NO 1
<211> LENGTH: 85
<212> TYPE: DNA
<213> ORGANISM: Artificial sequence
<220> FEATURE:
<223> OTHER INFORMATION: Synthetic tandem DNA {O-10A sequence}

<400> SEQUENCE: 1
ggtattttta caacaattac caacaacaac aaacaacaaa caacattaca attactattt      60
acaattacaa aaaaaaaaaa tgtct                                            85

<210> SEQ ID NO 2
<211> LENGTH: 146
<212> TYPE: DNA
<213> ORGANISM: Artificial sequence
<220> FEATURE:
<223> OTHER INFORMATION: Synthetic tandem DNA {KlFLO8-O-10A}

<400> SEQUENCE: 2
gagatagaga gagagattcc gtgttttgt ctcctgttct ttacacacgt attttcaacg       60 cggtatttt acaacaatta ccaacaacaa caaacaacaa acaacattac aattactatt      120
tacaattaca aaaaaaaaaa atgtct                                          146

<210> SEQ ID NO 3
<211> LENGTH: 147
<212> TYPE: DNA
<213> ORGANISM: Artificial sequence
<220> FEATURE:
<223> OTHER INFORMATION: Synthetic tandem DNA {KlMSN1-O-10A}

<400> SEQUENCE: 3
aacatagaaa tcatcatttt aattgattcg gtgttttcga gtctagtatt gattgtttaa      60
tcggtatttt tacaacaatt accaacaaca acaaacaaca aacaacatta caattactat    120
ttacaattac aaaaaaaaaa aatgtct                                         147

<210> SEQ ID NO 4
<211> LENGTH: 146
<212> TYPE: DNA
<213> ORGANISM: Artificial sequence
<220> FEATURE:
<223> OTHER INFORMATION: Synthetic tandem DNA {KlNCE102-O-10A}

<400> SEQUENCE: 4
aaaagaaatc tctcaagctg aaattaaacc aaaactctaa tataagaaaa aaaaatagaa      60
aggtattttt acaacaatta ccaacaacaa caaacaacaa acaacattac aattactatt    120
tacaattaca aaaaaaaaaa atgtct                                          146

<210> SEQ ID NO 5
<211> LENGTH: 146
<212> TYPE: DNA
<213> ORGANISM: Artificial sequence
<220> FEATURE:
<223> OTHER INFORMATION: Synthetic tandem DNA {KlBOI1-O-10A}
```

<400> SEQUENCE: 5

```
catttagagc atctcagccg tatcataccg ttcgagttcc agaaatacct acaaaatcag    60
tggtattttt acaacaatta ccaacaacaa caaacaacaa acaacattac aattactatt   120
tacaattaca aaaaaaaaaa atgtct                                        146
```

<210> SEQ ID NO 6
<211> LENGTH: 146
<212> TYPE: DNA
<213> ORGANISM: Artificial sequence
<220> FEATURE:
<223> OTHER INFORMATION: Synthetic tandem DNA {ScFLO8-O-10A}

<400> SEQUENCE: 6

```
aaaaaataaa cacgaagacg tttatagaca taaataaaga ggaaacgcat tccgtggtag    60 aggtatttt acaacaatta ccaacaacaa caaacaacaa acaacattac aattactatt   120
tacaattaca aaaaaaaaaa atgtct                                        146
```

<210> SEQ ID NO 7
<211> LENGTH: 146
<212> TYPE: DNA
<213> ORGANISM: Artificial sequence
<220> FEATURE:
<223> OTHER INFORMATION: Synthetic tandem DNA {ScMSN1-O-10A}

<400> SEQUENCE: 7

```
ccttgcttat aagaaaagaa accaaatcag aaaaggagat tatttcaagg taggcatcga    60 aggtatttt acaacaatta ccaacaacaa caaacaacaa acaacattac aattactatt   120
tacaattaca aaaaaaaaaa atgtct                                        146
```

<210> SEQ ID NO 8
<211> LENGTH: 146
<212> TYPE: DNA
<213> ORGANISM: Artificial sequence
<220> FEATURE:
<223> OTHER INFORMATION: Synthetic tandem DNA {ScNCE102-O-10A}

<400> SEQUENCE: 8

```
gaaaaatcgg ttaaaaaaac ttttcttctc aaagcatacc taataacaat ataatcccat    60 aggtatttt acaacaatta ccaacaacaa caaacaacaa acaacattac aattactatt   120
tacaattaca aaaaaaaaaa atgtct                                        146
```

<210> SEQ ID NO 9
<211> LENGTH: 146
<212> TYPE: DNA
<213> ORGANISM: Artificial sequence
<220> FEATURE:
<223> OTHER INFORMATION: Synthetic tandem DNA {ScBOI1-O-10A}

<400> SEQUENCE: 9

```
aatttcaaca aagttctaac tcgaggtgac cggaggccac tgtaataata aaaaatagaa    60 gggtatttt acaacaatta ccaacaacaa caaacaacaa acaacattac aattactatt   120
tacaattaca aaaaaaaaaa atgtct                                        146
```

<210> SEQ ID NO 10
<211> LENGTH: 146
<212> TYPE: DNA
<213> ORGANISM: Artificial sequence
<220> FEATURE:

<223> OTHER INFORMATION: Synthetic tandem DNA {O-K1FLO8-10A}

<400> SEQUENCE: 10 ggtatttta caacaattac caacaacaac aaacaacaaa caacattaca attactattt    60
acaattacag agatagagag agagattccg tgttttgtc tcctgttctt tacacacgta    120
ttttcaacgc aaaaaaaaaa atgtct    146

<210> SEQ ID NO 11
<211> LENGTH: 147
<212> TYPE: DNA
<213> ORGANISM: Artificial sequence
<220> FEATURE:
<223> OTHER INFORMATION: Synthetic tandem DNA {O-K1MSN1-10A}

<400> SEQUENCE: 11 ggtatttta caacaattac caacaacaac aaacaacaaa caacattaca attactattt    60
acaattacaa acatagaaat catcatttta attgattcgg tgttttcgag tctagtattg    120
attgtttaat caaaaaaaaa aatgtct    147

<210> SEQ ID NO 12
<211> LENGTH: 146
<212> TYPE: DNA
<213> ORGANISM: Artificial sequence
<220> FEATURE:
<223> OTHER INFORMATION: Synthetic tandem DNA {O-K1NCE102-10A}

<400> SEQUENCE: 12 ggtatttta caacaattac caacaacaac aaacaacaaa caacattaca attactattt    60
acaattacaa aaagaaatct ctcaagctga aattaaacca aaactctaat ataagaaaaa    120
aaaatagaaa aaaaaaaaaa atgtct    146

<210> SEQ ID NO 13
<211> LENGTH: 146
<212> TYPE: DNA
<213> ORGANISM: Artificial sequence
<220> FEATURE:
<223> OTHER INFORMATION: Synthetic tandem DNA {O-K1BOI1-10A}

<400> SEQUENCE: 13 ggtatttta caacaattac caacaacaac aaacaacaaa caacattaca attactattt    60
acaattacac atttagagca tctcagccgt atcataccgt tcgagttcca gaaataccta    120
caaaatcagt aaaaaaaaaa atgtct    146

<210> SEQ ID NO 14
<211> LENGTH: 146
<212> TYPE: DNA
<213> ORGANISM: Artificial sequence
<220> FEATURE:
<223> OTHER INFORMATION: Synthetic tandem DNA {O-ScFLO8-10A}

<400> SEQUENCE: 14 ggtatttta caacaattac caacaacaac aaacaacaaa caacattaca attactattt    60
acaattacaa aaaataaac acgaagacgt ttatagacat aaataaagag gaaacgcatt    120
ccgtggtaga aaaaaaaaaa atgtct    146

<210> SEQ ID NO 15
<211> LENGTH: 146
<212> TYPE: DNA
<213> ORGANISM: Artificial sequence

```
<220> FEATURE:
<223> OTHER INFORMATION: Synthetic tandem DNA {O-ScMSN1-10A}

<400> SEQUENCE: 15
ggtattttta caacaattac caacaacaac aaacaacaaa caacattaca attactattt      60
acaattacac cttgcttata agaaaagaaa ccaaatcaga aaaggagatt atttcaaggt     120
aggcatcgaa aaaaaaaaaa atgtct                                         146

<210> SEQ ID NO 16
<211> LENGTH: 146
<212> TYPE: DNA
<213> ORGANISM: Artificial sequence
<220> FEATURE:
<223> OTHER INFORMATION: Synthetic tandem DNA {O-ScNCE102-10A}

<400> SEQUENCE: 16
ggtattttta caacaattac caacaacaac aaacaacaaa caacattaca attactattt      60
acaattacag aaaaatcggt taaaaaaact tttcttctca aagcatacct aataacaata    120
taatcccata aaaaaaaaaa atgtct                                         146

<210> SEQ ID NO 17
<211> LENGTH: 146
<212> TYPE: DNA
<213> ORGANISM: Artificial sequence
<220> FEATURE:
<223> OTHER INFORMATION: Synthetic tandem DNA {O-ScBOI1-10A}

<400> SEQUENCE: 17
ggtattttta caacaattac caacaacaac aaacaacaaa caacattaca attactattt      60
acaattacaa atttcaacaa agttctaact cgaggtgacc ggaggccact gtaataataa    120
aaaatagaag aaaaaaaaaa atgtct                                         146

<210> SEQ ID NO 18
<211> LENGTH: 34
<212> TYPE: DNA
<213> ORGANISM: Artificial sequence
<220> FEATURE:
<223> OTHER INFORMATION: Synthetic DNA {Forward primer PF_FLO8KL_Omega}

<400> SEQUENCE: 18
cgtattttca acgcggtatt tttacaacaa ttac                                 34

<210> SEQ ID NO 19
<211> LENGTH: 35
<212> TYPE: DNA
<213> ORGANISM: Artificial sequence
<220> FEATURE:
<223> OTHER INFORMATION: Synthetic DNA {Reverse primer PR_FLO8KL_T7pro}

<400> SEQUENCE: 19
ctctctctct atctccctat agtgagtcgt attaa                                35

<210> SEQ ID NO 20
<211> LENGTH: 32
<212> TYPE: DNA
<213> ORGANISM: Artificial sequence
<220> FEATURE:
<223> OTHER INFORMATION: Synthetic DNA {Forward primer PF_T7pro_FLO8KL}

<400> SEQUENCE: 20
actcactata gggagataga gagagagatt cc                                   32
```

<210> SEQ ID NO 21
<211> LENGTH: 32
<212> TYPE: DNA
<213> ORGANISM: Artificial sequence
<220> FEATURE:
<223> OTHER INFORMATION: Synthetic DNA {Reverse primer PR_Omega_FLO8KL}

<400> SEQUENCE: 21
tgtaaaaata ccgcgttgaa aatacgtgtg ta                           32

<210> SEQ ID NO 22
<211> LENGTH: 36
<212> TYPE: DNA
<213> ORGANISM: Artificial sequence
<220> FEATURE:
<223> OTHER INFORMATION: Synthetic DNA {Forward primer PF_MSN1KL_Omega}

<400> SEQUENCE: 22
gattgtttaa tcggtatttt tacaacaatt accaac                       36

<210> SEQ ID NO 23
<211> LENGTH: 32
<212> TYPE: DNA
<213> ORGANISM: Artificial sequence
<220> FEATURE:
<223> OTHER INFORMATION: Synthetic DNA {Reverse primer PR_MSN1KL_T7pro}

<400> SEQUENCE: 23
ctatgttcct atagtgagtc gtattaattt cg                           32

<210> SEQ ID NO 24
<211> LENGTH: 37
<212> TYPE: DNA
<213> ORGANISM: Artificial sequence
<220> FEATURE:
<223> OTHER INFORMATION: Synthetic DNA {Forward primer PF_T7pro_MSN1KL}

<400> SEQUENCE: 24
acgactcact ataggaacat agaaatcatc attttaa                      37

<210> SEQ ID NO 25
<211> LENGTH: 38
<212> TYPE: DNA
<213> ORGANISM: Artificial sequence
<220> FEATURE:
<223> OTHER INFORMATION: Synthetic DNA {Reverse primer PR_Omega_MSN1KL}

<400> SEQUENCE: 25
gttgtaaaaa taccgattaa acaatcaata ctagactc                     38

<210> SEQ ID NO 26
<211> LENGTH: 36
<212> TYPE: DNA
<213> ORGANISM: Artificial sequence
<220> FEATURE:
<223> OTHER INFORMATION: Synthetic DNA {Forward primer
      PF_KLNCE102_Omega}

<400> SEQUENCE: 26
tagaaaggta ttttacaac aattaccaac aacaac                        36

<210> SEQ ID NO 27
<211> LENGTH: 38
<212> TYPE: DNA
<213> ORGANISM: Artificial sequence
<220> FEATURE:

<223> OTHER INFORMATION: Synthetic DNA {Reverse primer
      PR_KLNCE102_T7pro}

<400> SEQUENCE: 27
gagatttctt ttcctatagt gagtcgtatt aatttcgc                              38

<210> SEQ ID NO 28
<211> LENGTH: 33
<212> TYPE: DNA
<213> ORGANISM: Artificial sequence
<220> FEATURE:
<223> OTHER INFORMATION: Synthetic DNA {Forward primer
      PF_T7pro_KLNCE102}

<400> SEQUENCE: 28
gactcactat aggaaaagaa atctctcaag ctg                                   33

<210> SEQ ID NO 29
<211> LENGTH: 42
<212> TYPE: DNA
<213> ORGANISM: Artificial sequence
<220> FEATURE:
<223> OTHER INFORMATION: Synthetic DNA {Reverse primer
      PR_Omega_KLNCE102}

<400> SEQUENCE: 29
gtaattgttg taaaatacc tttctatttt tttttcttat at                          42

<210> SEQ ID NO 30
<211> LENGTH: 35
<212> TYPE: DNA
<213> ORGANISM: Artificial sequence
<220> FEATURE:
<223> OTHER INFORMATION: Synthetic DNA {Forward primer PF_BOI1KL_Omega}

<400> SEQUENCE: 30
cctacaaaat cagtggtatt tttacaacaa ttacc                                 35

<210> SEQ ID NO 31
<211> LENGTH: 32
<212> TYPE: DNA
<213> ORGANISM: Artificial sequence
<220> FEATURE:
<223> OTHER INFORMATION: Synthetic DNA {Reverse primer PR_BOI1KL_T7pro}

<400> SEQUENCE: 31
gctctaaatg cctatagtga gtcgtattaa tt                                    32

<210> SEQ ID NO 32
<211> LENGTH: 30
<212> TYPE: DNA
<213> ORGANISM: Artificial sequence
<220> FEATURE:
<223> OTHER INFORMATION: Synthetic DNA {Forward primer PF_T7pro_BOI1KL}

<400> SEQUENCE: 32
tcactatagg catttagagc atctcagccg                                       30

<210> SEQ ID NO 33
<211> LENGTH: 38
<212> TYPE: DNA
<213> ORGANISM: Artificial sequence
<220> FEATURE:
<223> OTHER INFORMATION: Synthetic DNA {Reverse primer PR_Omega_BOI1KL}

<400> SEQUENCE: 33
ttgttgtaaa ataccactg attttgtagg tatttctg        38

<210> SEQ ID NO 34
<211> LENGTH: 30
<212> TYPE: DNA
<213> ORGANISM: Artificial sequence
<220> FEATURE:
<223> OTHER INFORMATION: Synthetic DNA {Forward primer PF_FLO8_Omega}

<400> SEQUENCE: 34
ccgtggtaga ggtatttta caacaattac        30

<210> SEQ ID NO 35
<211> LENGTH: 34
<212> TYPE: DNA
<213> ORGANISM: Artificial sequence
<220> FEATURE:
<223> OTHER INFORMATION: Synthetic DNA {Reverse primer PR_FLO8_T7pro}

<400> SEQUENCE: 35
cgtgtttatt ttttcctata gtgagtcgta ttaa        34

<210> SEQ ID NO 36
<211> LENGTH: 31
<212> TYPE: DNA
<213> ORGANISM: Artificial sequence
<220> FEATURE:
<223> OTHER INFORMATION: Synthetic DNA {Forward primer PF_T7pro_FLO8}

<400> SEQUENCE: 36
ctcactatag gaaaaataa acacgaagac g        31

<210> SEQ ID NO 37
<211> LENGTH: 30
<212> TYPE: DNA
<213> ORGANISM: Artificial sequence
<220> FEATURE:
<223> OTHER INFORMATION: Synthetic DNA {Reverse primer PR_Omega_FLO8}

<400> SEQUENCE: 37
taaaaatacc tctaccacgg aatgcgtttc        30

<210> SEQ ID NO 38
<211> LENGTH: 33
<212> TYPE: DNA
<213> ORGANISM: Artificial sequence
<220> FEATURE:
<223> OTHER INFORMATION: Synthetic DNA {Forward primer PF_MSN1_Omega}

<400> SEQUENCE: 38
ggtaggcatc gaaggtattt ttacaacaat tac        33

<210> SEQ ID NO 39
<211> LENGTH: 31
<212> TYPE: DNA
<213> ORGANISM: Artificial sequence
<220> FEATURE:
<223> OTHER INFORMATION: Synthetic DNA {Reverse primer PR_MSN1_T7pro}

<400> SEQUENCE: 39
agcaaggcct atagtgagtc gtattaattt c        31

<210> SEQ ID NO 40
<211> LENGTH: 35
<212> TYPE: DNA
<213> ORGANISM: Artificial sequence

```
<220> FEATURE:
<223> OTHER INFORMATION: Synthetic DNA {Forward primer PF_T7pro_MSN1}

<400> SEQUENCE: 40
gactcactat aggccttgct tataagaaaa gaaac                              35

<210> SEQ ID NO 41
<211> LENGTH: 34
<212> TYPE: DNA
<213> ORGANISM: Artificial sequence
<220> FEATURE:
<223> OTHER INFORMATION: Synthetic DNA {Reverse primer PR_Omega_MSN1}

<400> SEQUENCE: 41
gttgtaaaaa taccttcgat gcctaccttg aaat                               34

<210> SEQ ID NO 42
<211> LENGTH: 36
<212> TYPE: DNA
<213> ORGANISM: Artificial sequence
<220> FEATURE:
<223> OTHER INFORMATION: Synthetic DNA {Forward primer PF_NCE102_Omega}

<400> SEQUENCE: 42
caatataatc ccataggtat ttttacaaca attacc                             36

<210> SEQ ID NO 43
<211> LENGTH: 34
<212> TYPE: DNA
<213> ORGANISM: Artificial sequence
<220> FEATURE:
<223> OTHER INFORMATION: Synthetic DNA {Reverse primer PR_NCE102_T7pro}

<400> SEQUENCE: 43 ccgattttc cctatagtga gtcgtattaa tttc                                34

<210> SEQ ID NO 44
<211> LENGTH: 34
<212> TYPE: DNA
<213> ORGANISM: Artificial sequence
<220> FEATURE:
<223> OTHER INFORMATION: Synthetic DNA {Forward primer PF_T7pro_NCE102}

<400> SEQUENCE: 44
cgactcacta tagggaaaaa tcggttaaaa aaac                               34

<210> SEQ ID NO 45
<211> LENGTH: 37
<212> TYPE: DNA
<213> ORGANISM: Artificial sequence
<220> FEATURE:
<223> OTHER INFORMATION: Synthetic DNA {Reverse primer PR_Omega_NCE102}

<400> SEQUENCE: 45
gttgtaaaaa tacctatggg attatattgt tattagg                            37

<210> SEQ ID NO 46
<211> LENGTH: 40
<212> TYPE: DNA
<213> ORGANISM: Artificial sequence
<220> FEATURE:
<223> OTHER INFORMATION: Synthetic DNA {Forward primer PF_BOI1_Omega}

<400> SEQUENCE: 46
taataaaaaa tagaagggta ttttacaac aattaccaac                          40
```

<210> SEQ ID NO 47
<211> LENGTH: 34
<212> TYPE: DNA
<213> ORGANISM: Artificial sequence
<220> FEATURE:
<223> OTHER INFORMATION: Synthetic DNA {Reverse primer PR_BOI1_T7pro}

<400> SEQUENCE: 47
ctttgttgaa attcctatag tgagtcgtat taat                           34

<210> SEQ ID NO 48
<211> LENGTH: 36
<212> TYPE: DNA
<213> ORGANISM: Artificial sequence
<220> FEATURE:
<223> OTHER INFORMATION: Synthetic DNA {Forward primer PF_T7pro_BOI1}

<400> SEQUENCE: 48
tacgactcac tataggaatt caacaaagt tctaac                          36

<210> SEQ ID NO 49
<211> LENGTH: 40
<212> TYPE: DNA
<213> ORGANISM: Artificial sequence
<220> FEATURE:
<223> OTHER INFORMATION: Synthetic DNA {Reverse primer PR_Omega_BOI1}

<400> SEQUENCE: 49
gtaattgttg taaaaatacc cttctatttt ttattattac                     40

<210> SEQ ID NO 50
<211> LENGTH: 38
<212> TYPE: DNA
<213> ORGANISM: Artificial sequence
<220> FEATURE:
<223> OTHER INFORMATION: Synthetic DNA {Forward primer O-Flo8(KL)_PF-2}

<400> SEQUENCE: 50
caacgcaaaa aaaaaaatgt ctgaagacgc caaaaaca                       38

<210> SEQ ID NO 51
<211> LENGTH: 41
<212> TYPE: DNA
<213> ORGANISM: Artificial sequence
<220> FEATURE:
<223> OTHER INFORMATION: Synthetic DNA {Reverse primer O-Flo8(KL)-PR-2}

<400> SEQUENCE: 51
gaatctctct ctctatctct gtaattgtaa atagtaattg t                   41

<210> SEQ ID NO 52
<211> LENGTH: 44
<212> TYPE: DNA
<213> ORGANISM: Artificial sequence
<220> FEATURE:
<223> OTHER INFORMATION: Synthetic DNA {Forward primer Flo8(KL)_F}

<400> SEQUENCE: 52
acaattacta tttacaatta cagagataga gagagagatt ccgt                44

<210> SEQ ID NO 53
<211> LENGTH: 55
<212> TYPE: DNA
<213> ORGANISM: Artificial sequence
<220> FEATURE:
<223> OTHER INFORMATION: Synthetic DNA {Reverse primer Flo8(KL)_R}

<400> SEQUENCE: 53
gtttttggcg tcttcagaca ttttttttt tgcgttgaaa atacgtgtgt aaaga    55

<210> SEQ ID NO 54
<211> LENGTH: 33
<212> TYPE: DNA
<213> ORGANISM: Artificial sequence
<220> FEATURE:
<223> OTHER INFORMATION: Synthetic DNA {Forward primer
     PF_pET21a_KLMSN1_10A}

<400> SEQUENCE: 54
gtttaatcaa aaaaaaaaat gtctgaagac gcc    33

<210> SEQ ID NO 55
<211> LENGTH: 45
<212> TYPE: DNA
<213> ORGANISM: Artificial sequence
<220> FEATURE:
<223> OTHER INFORMATION: Synthetic DNA {Reverse primer
     PR_pET21a_KLMSN1_Omega}

<400> SEQUENCE: 55
gatttctatg tttgtaattg taaatagtaa ttgtaatgtt gtttg    45

<210> SEQ ID NO 56
<211> LENGTH: 42
<212> TYPE: DNA
<213> ORGANISM: Artificial sequence
<220> FEATURE:
<223> OTHER INFORMATION: Synthetic DNA {Forward primer
     PF_KLMSN1_Omega_pET21a}

<400> SEQUENCE: 56
caattactat ttacaattac aaacatagaa atcatcattt ta    42

<210> SEQ ID NO 57
<211> LENGTH: 37
<212> TYPE: DNA
<213> ORGANISM: Artificial sequence
<220> FEATURE:
<223> OTHER INFORMATION: Synthetic DNA {Reverse primer
     PR_KLMSN1_10A_pET21a}

<400> SEQUENCE: 57
cagacatttt tttttttgat taaacaatca atactag    37

<210> SEQ ID NO 58
<211> LENGTH: 22
<212> TYPE: DNA
<213> ORGANISM: Artificial sequence
<220> FEATURE:
<223> OTHER INFORMATION: Synthetic DNA {Forward primer O-IRES-PF}

<400> SEQUENCE: 58
atgtctgaag acgccaaaaa ca    22

<210> SEQ ID NO 59
<211> LENGTH: 22
<212> TYPE: DNA
<213> ORGANISM: Artificial sequence
<220> FEATURE:
<223> OTHER INFORMATION: Synthetic DNA {Reverse primer O-IRES-PR}

<400> SEQUENCE: 59
tgtaattgta aatagtaatt gt                                             22

<210> SEQ ID NO 60
<211> LENGTH: 42
<212> TYPE: DNA
<213> ORGANISM: Artificial sequence
<220> FEATURE:
<223> OTHER INFORMATION: Synthetic DNA {Forward primer NCE102(KL)-F}

<400> SEQUENCE: 60
aattactatt tacaattaca aaaagaaatc tctcaagctg aa                       42

<210> SEQ ID NO 61
<211> LENGTH: 54
<212> TYPE: DNA
<213> ORGANISM: Artificial sequence
<220> FEATURE:
<223> OTHER INFORMATION: Synthetic DNA {Reverse primer NCE102(KL)-R}

<400> SEQUENCE: 61 gttttttggcg tcttcagaca tttttttttt ttttctattt tttttcctta tatt         54

<210> SEQ ID NO 62
<211> LENGTH: 29
<212> TYPE: DNA
<213> ORGANISM: Artificial sequence
<220> FEATURE:
<223> OTHER INFORMATION: Synthetic DNA {Forward primer
      PF_pET21a_10A_KLBOI}

<400> SEQUENCE: 62
cagtaaaaaa aaaatgtctg aagacgcca                                      29

<210> SEQ ID NO 63
<211> LENGTH: 41
<212> TYPE: DNA
<213> ORGANISM: Artificial sequence
<220> FEATURE:
<223> OTHER INFORMATION: Synthetic DNA {Reverse primer
      PR_pET21a_Omega_KLBOI}

<400> SEQUENCE: 63
gagatgctct aaatgtgtaa ttgtaaatag taattgtaat g                        41

<210> SEQ ID NO 64
<211> LENGTH: 35
<212> TYPE: DNA
<213> ORGANISM: Artificial sequence
<220> FEATURE:
<223> OTHER INFORMATION: Synthetic DNA {Forward primer
      PF_KLBOI_Omega_pET21a}

<400> SEQUENCE: 64
ctatttacaa ttacacattt agagcatctc agccg                               35

<210> SEQ ID NO 65
<211> LENGTH: 40
<212> TYPE: DNA
<213> ORGANISM: Artificial sequence
<220> FEATURE:
<223> OTHER INFORMATION: Synthetic DNA {Reverse primer
      PR_KLBOI_10A_pET21a}

<400> SEQUENCE: 65
cagacatttt ttttttact gattttgtag gtatttctgg                           40

<210> SEQ ID NO 66
<211> LENGTH: 43
<212> TYPE: DNA
<213> ORGANISM: Artificial sequence
<220> FEATURE:
<223> OTHER INFORMATION: Synthetic DNA {Forward primer O-FLO8-PF-2}

<400> SEQUENCE: 66
tccgtggtag aaaaaaaaaa aatgtctgaa gacgccaaaa aca            43

<210> SEQ ID NO 67
<211> LENGTH: 42
<212> TYPE: DNA
<213> ORGANISM: Artificial sequence
<220> FEATURE:
<223> OTHER INFORMATION: Synthetic DNA {Reverse primer O-FLO8-PR-2}

<400> SEQUENCE: 67
cgtcttcgtg tttatttttt tgtaattgta aatagtaatt gt             42

<210> SEQ ID NO 68
<211> LENGTH: 44
<212> TYPE: DNA
<213> ORGANISM: Artificial sequence
<220> FEATURE:
<223> OTHER INFORMATION: Synthetic DNA {Forward primer Flo8_F}

<400> SEQUENCE: 68
acaattacta tttacaatta caaaaaaata aacacgaaga cgtt           44

<210> SEQ ID NO 69
<211> LENGTH: 53
<212> TYPE: DNA
<213> ORGANISM: Artificial sequence
<220> FEATURE:
<223> OTHER INFORMATION: Synthetic DNA {Reverse primer Flo8_R}

<400> SEQUENCE: 69 tgttttggc gtcttcagac attttttttt tttctaccac ggaatgcgtt tcc  53

<210> SEQ ID NO 70
<211> LENGTH: 34
<212> TYPE: DNA
<213> ORGANISM: Artificial sequence
<220> FEATURE:
<223> OTHER INFORMATION: Synthetic DNA {Forward primer
       PF_pET21a_MSN1_10A}

<400> SEQUENCE: 70
atcgaaaaaa aaaaaaatgt ctgaagacgc caaa                      34

<210> SEQ ID NO 71
<211> LENGTH: 39
<212> TYPE: DNA
<213> ORGANISM: Artificial sequence
<220> FEATURE:
<223> OTHER INFORMATION: Synthetic DNA {Reverse primer
       PR_pET21a_MSN1_Omega}

<400> SEQUENCE: 71
ataagcaagg tgtaattgta aatagtaatt gtaatgttg                 39

<210> SEQ ID NO 72
<211> LENGTH: 41
<212> TYPE: DNA
<213> ORGANISM: Artificial sequence
<220> FEATURE:

```
<223> OTHER INFORMATION: Synthetic DNA {Forward primer
      PF_MSN1_Omega_pET21a}

<400> SEQUENCE: 72
caattactat ttacaattac accttgctta taagaaaaga a                        41

<210> SEQ ID NO 73
<211> LENGTH: 39
<212> TYPE: DNA
<213> ORGANISM: Artificial sequence
<220> FEATURE:
<223> OTHER INFORMATION: Synthetic DNA {Reverse primer
      PR_MSN1_10A_pET21a}

<400> SEQUENCE: 73
cagacatttt ttttttttc gatgcctacc ttgaaataa                            39

<210> SEQ ID NO 74
<211> LENGTH: 31
<212> TYPE: DNA
<213> ORGANISM: Artificial sequence
<220> FEATURE:
<223> OTHER INFORMATION: Synthetic DNA {Forward primer O-IRES-PF2}

<400> SEQUENCE: 74
atgtctgaag acgccaaaaa cataaagaaa g                                   31

<210> SEQ ID NO 75
<211> LENGTH: 41
<212> TYPE: DNA
<213> ORGANISM: Artificial sequence
<220> FEATURE:
<223> OTHER INFORMATION: Synthetic DNA {Reverse primer O-IRES-PR2}

<400> SEQUENCE: 75
tgtaattgta aatagtaatt gtaatgttgt ttgttgtttg t                        41

<210> SEQ ID NO 76
<211> LENGTH: 44
<212> TYPE: DNA
<213> ORGANISM: Artificial sequence
<220> FEATURE:
<223> OTHER INFORMATION: Synthetic DNA {Forward primer NCE102-F}

<400> SEQUENCE: 76
acaattacta tttacaatta cagaaaaatc ggttaaaaaa actt                     44

<210> SEQ ID NO 77
<211> LENGTH: 54
<212> TYPE: DNA
<213> ORGANISM: Artificial sequence
<220> FEATURE:
<223> OTHER INFORMATION: Synthetic DNA {Reverse primer NCE102-R}

<400> SEQUENCE: 77 tgttttttggc gtcttcagac attttttttt tttatgggat tatattgtta ttag         54

<210> SEQ ID NO 78
<211> LENGTH: 31
<212> TYPE: DNA
<213> ORGANISM: Artificial sequence
<220> FEATURE:
<223> OTHER INFORMATION: Synthetic DNA {Forward primer
      PF_pET21a_10A_BOI1}

<400> SEQUENCE: 78
```
tagaagaaaa aaaaaaatgt ctgaagacgc c                                          31

<210> SEQ ID NO 79
<211> LENGTH: 38
<212> TYPE: DNA
<213> ORGANISM: Artificial sequence
<220> FEATURE:
<223> OTHER INFORMATION: Synthetic DNA {Reverse primer
      PR_pET21a_Omega_BOI1}

<400> SEQUENCE: 79
gttgaaattt gtaattgtaa atagtaattg taatgttg                                    38

<210> SEQ ID NO 80
<211> LENGTH: 41
<212> TYPE: DNA
<213> ORGANISM: Artificial sequence
<220> FEATURE:
<223> OTHER INFORMATION: Synthetic DNA {Forward primer
      PF_BOI1_Omega_pET21a}

<400> SEQUENCE: 80
caattactat ttacaattac aaatttcaac aaagttctaa c                                41

<210> SEQ ID NO 81
<211> LENGTH: 41
<212> TYPE: DNA
<213> ORGANISM: Artificial sequence
<220> FEATURE:
<223> OTHER INFORMATION: Synthetic DNA {Reverse primer
      PR_BOI1_10A_pET21a}

<400> SEQUENCE: 81
tcttcagaca tttttttttt tcttctattt tttattatta c                                41

<210> SEQ ID NO 82
<211> LENGTH: 27
<212> TYPE: DNA
<213> ORGANISM: Artificial sequence
<220> FEATURE:
<223> OTHER INFORMATION: Synthetic DNA {Forward primer T7_pET21a_F}

<400> SEQUENCE: 82
cgcgaaatta atacgactca ctatagg                                                27

<210> SEQ ID NO 83
<211> LENGTH: 24
<212> TYPE: DNA
<213> ORGANISM: Artificial sequence
<220> FEATURE:
<223> OTHER INFORMATION: Synthetic DNA {Reverse primer T7ter_pET21a_R}

<400> SEQUENCE: 83
tccggatata gttcctcctt tcag                                                   24

<210> SEQ ID NO 84
<211> LENGTH: 16
<212> TYPE: RNA
<213> ORGANISM: Artificial sequence
<220> FEATURE:
<223> OTHER INFORMATION: Synthetic DNA {A Kozak sequence}

<400> SEQUENCE: 84
aaaaaaaaaa augucu                                                            16

<210> SEQ ID NO 85

<211> LENGTH: 1799
<212> TYPE: DNA
<213> ORGANISM: Artificial sequence
<220> FEATURE:
<223> OTHER INFORMATION: Synthetic DNA {plasmid K1NCE102-O-10A-Fluc}

<400> SEQUENCE: 85

| | | | | | |
|---|---|---|---|---|---|
| aaaagaaatc | tctcaagctg | aaattaaacc | aaaactctaa | tataagaaaa | aaaaatagaa | 60 |
| aggtattttt | acaacaatta | ccaacaacaa | caaacaacaa | acaacattac | aattactatt | 120 |
| tacaattaca | aaaaaaaaa | atgtctgaag | acgccaaaaa | cataaagaaa | ggcccggcgc | 180 |
| cattctatcc | tctagaggat | ggaaccgctg | gagagcaact | gcataaggct | atgaagagat | 240 |
| acgccctggt | tcctggaaca | attgctttta | cagatgcaca | tatcgaggtg | aacatcacgt | 300 |
| acgcggaata | cttcgaaatg | tccgttcggt | tggcagaagc | tatgaaacga | tatgggctga | 360 |
| atacaaatca | cagaatcgtc | gtatgcagtg | aaaactctct | tcaattcttt | atgccggtgt | 420 |
| tgggcgcgtt | atttatcgga | gttgcagttg | cgcccgcgaa | cgacatttat | aatgaacgtg | 480 |
| aattgctcaa | cagtatgaac | atttcgcagc | ctaccgtagt | gtttgtttcc | aaaaagggggt | 540 |
| tgcaaaaaat | tttgaacgtg | caaaaaaaat | taccaataat | ccagaaaatt | attatcatgg | 600 |
| attctaaaac | ggattaccag | ggatttcagt | cgatgtacac | gttcgtcaca | tctcatctac | 660 |
| ctcccggttt | taatgaatac | gattttgtac | cagagtcctt | tgatcgtgac | aaaacaattg | 720 |
| cactgataat | gaattcctct | ggatctactg | ggttacctaa | gggtgtggcc | cttccgcata | 780 |
| gaactgcctg | cgtcagattc | tcgcatgcca | gagatcctat | ttttggcaat | caaatcattc | 840 |
| cggatactgc | gattttaagt | gttgttccat | tccatcacgg | ttttggaatg | tttactacac | 900 |
| tcggatattt | gatatgtgga | tttcgagtcg | tcttaatgta | tagatttgaa | gaagagctgt | 960 |
| ttttacgatc | ccttcaggat | tacaaaattc | aaagtgcgtt | gctagtacca | accctatttt | 1020 |
| cattcttcgc | caaaagcact | ctgattgaca | aatacgattt | atctaattta | cacgaaattg | 1080 |
| cttctggggg | cgcacctctt | tcgaaagaag | tcggggaagc | ggttgcaaaa | cgcttccatc | 1140 |
| ttccagggat | acgacaagga | tatgggctca | ctgagactac | atcagctatt | ctgattacac | 1200 |
| ccgaggggga | tgataaaccg | ggcgcggtcg | gtaaagttgt | tccatttttt | gaagcgaagg | 1260 |
| ttgtggatct | ggataccggg | aaaacgctgg | gcgttaatca | gagaggcgaa | ttatgtgtca | 1320 |
| gaggacctat | gattatgtcc | ggttatgtaa | acaatccgga | agcgaccaac | gccttgattg | 1380 |
| acaaggatgg | atggctacat | tctggagaca | tagcttactg | ggacgaagac | gaacacttct | 1440 |
| tcatagttga | ccgcttgaag | tctttaatta | aatacaaagg | atatcaggtg | gcccccgctg | 1500 |
| aattggaatc | gatattgtta | caacacccca | acatcttcga | cgcgggcgtg | gcaggtcttc | 1560 |
| ccgacgatga | cgccggtgaa | cttcccgccg | ccgttgttgt | tttggagcac | ggaaagacga | 1620 |
| tgacggaaaa | agagatcgtg | gattacgtcg | ccagtcaagt | aacaaccgcg | aaaaagttgc | 1680 |
| gcggaggagt | tgtgtttgtg | gacgaagtac | cgaaaggtct | taccggaaaa | ctcgacgcaa | 1740 |
| gaaaaatcag | agagatcctc | ataaaggcca | agaagggcgg | aaagtccaaa | ttggtttaa | 1799 |

<210> SEQ ID NO 86
<211> LENGTH: 1799
<212> TYPE: DNA
<213> ORGANISM: Artificial sequence
<220> FEATURE:
<223> OTHER INFORMATION: Synthetic DNA {plasmid ScFLO8-O-10A-Fluc}

<400> SEQUENCE: 86

| | | | | | |
|---|---|---|---|---|---|
| aaaaaataaa | cacgaagacg | tttatagaca | taaataaaga | ggaaacgcat | tccgtggtag | 60 |

```
aggtatttt   acaacaatta   ccaacaacaa   caaacaacaa   acaacattac   aattactatt       120
tacaattaca   aaaaaaaaaa   atgtctgaag   acgccaaaaa   cataaagaaa   ggcccggcgc       180
cattctatcc   tctagaggat   ggaaccgctg   gagagcaact   gcataaggct   atgaagagat       240
acgccctggt   tcctggaaca   attgctttta   cagatgcaca   tatcgaggtg   aacatcacgt       300
acgcggaata   cttcgaaatg   tccgttcggt   tggcagaagc   tatgaaacga   tatgggctga       360
atacaaatca   cagaatcgtc   gtatgcagtg   aaaactctct   tcaattcttt   atgccggtgt       420
tgggcgcgtt   atttatcgga   gttgcagttg   cgcccgcgaa   cgacatttat   aatgaacgtg       480
aattgctcaa   cagtatgaac   atttcgcagc   ctaccgtagt   gtttgtttcc   aaaaaggggt       540
tgcaaaaaat   tttgaacgtg   caaaaaaaat   taccaataat   ccagaaaatt   attatcatgg       600
attctaaaac   ggattaccag   ggatttcagt   cgatgtacac   gttcgtcaca   tctcatctac       660
ctcccggttt   taatgaatac   gattttgtac   cagagtcctt   tgatcgtgac   aaaacaattg       720
cactgataat   gaattcctct   ggatctactg   ggttacctaa   gggtgtggcc   cttccgcata       780
gaactgcctg   cgtcagattc   tcgcatgcca   gagatcctat   ttttggcaat   caaatcattc       840
cggatactgc   gattttaagt   gttgttccat   tccatcacgg   ttttggaatg   tttactacac       900
tcggatattt   gatatgtgga   tttcgagtcg   tcttaatgta   tagatttgaa   gaagagctgt       960
ttttacgatc   ccttcaggat   tacaaaattc   aaagtgcgtt   gctagtacca   accctatttt      1020
cattcttcgc   caaaagcact   ctgattgaca   aatacgattt   atctaattta   cacgaaattg      1080
cttctggggg   cgcacctctt   tcgaaagaag   tcggggaagc   ggttgcaaaa   cgcttccatc      1140
ttccagggat   acgacaagga   tatgggctca   ctgagactac   atcagctatt   ctgattacac      1200
ccgaggggga   tgataaaccg   ggcgcggtcg   gtaaagttgt   tccattttt   gaagcgaagg       1260 ttgtggatct   ggataccggg   aaaacgctgg   gcgttaatca   gagaggcgaa   ttatgtgtca      1320
gaggacctat   gattatgtcc   ggttatgtaa   acaatccgga   agcgaccaac   gccttgattg      1380
acaaggatgg   atggctacat   tctggagaca   tagcttactg   ggacgaagac   gaacacttct      1440
tcatagttga   ccgcttgaag   tctttaatta   aatacaaagg   atatcaggtg   gcccccgctg      1500
aattggaatc   gatattgtta   caacacccca   acatcttcga   cgcgggcgtg   gcaggtcttc      1560
ccgacgatga   cgccggtgaa   cttcccgccg   ccgttgttgt   tttggagcac   ggaaagacga      1620
tgacggaaaa   agagatcgtg   gattacgtcg   ccagtcaagt   aacaaccgcg   aaaaagttgc      1680
gcggaggagt   tgtgtttgtg   gacgaagtac   cgaaaggtct   taccggaaaa   ctcgacgcaa      1740
gaaaaatcag   agagatcctc   ataaaggcca   agaagggcgg   aaagtccaaa   ttggtttaa       1799
```

<210> SEQ ID NO 87
<211> LENGTH: 1800
<212> TYPE: DNA
<213> ORGANISM: Artificial sequence
<220> FEATURE:
<223> OTHER INFORMATION: Synthetic DNA {plasmid K1MSN1-O-10A-Fluc}

<400> SEQUENCE: 87

```
aacatagaaa   tcatcatttt   aattgattcg   gtgttttcga   gtctagtatt   gattgtttaa        60
tcggtatttt   tacaacaatt   accaacaaca   acaacaacaa   aacaacatta   caattactat       120
ttacaattac   aaaaaaaaaa   aatgtctgaa   gacgccaaaa   acataaagaa   aggcccggcg       180
ccattctatc   ctctagagga   tggaaccgct   ggagagcaac   tgcataaggc   tatgaagaga       240
tacgccctgg   ttcctggaac   aattgctttt   acagatgcac   atatcgaggt   gaacatcacg       300
```

```
tacgcggaat acttcgaaat gtccgttcgg ttggcagaag ctatgaaacg atatgggctg    360
aatacaaatc acagaatcgt cgtatgcagt gaaaactctc ttcaattctt tatgccggtg    420
ttgggcgcgt tatttatcgg agttgcagtt gcgcccgcga acgacattta taatgaacgt    480
gaattgctca acagtatgaa catttcgcag cctaccgtag tgtttgtttc caaaaagggg    540
ttgcaaaaaa ttttgaacgt gcaaaaaaaa ttaccaataa tccagaaaat tattatcatg    600
gattctaaaa cggattacca gggatttcag tcgatgtaca cgttcgtcac atctcatcta    660
cctcccggtt ttaatgaata cgattttgta ccagagtcct ttgatcgtga caaaacaatt    720
gcactgataa tgaattcctc tggatctact gggttaccta agggtgtggc ccttccgcat    780
agaactgcct gcgtcagatt ctcgcatgcc agagatccta tttttggcaa tcaaatcatt    840
ccggatactg cgattttaag tgttgttcca ttccatcacg gttttggaat gtttactaca    900
ctcggatatt tgatatgtgg atttcgagtc gtcttaatgt atagatttga agaagagctg    960
tttttacgat cccttcagga ttacaaaatt caaagtgcgt tgctagtacc aaccctattt   1020
tcattcttcg ccaaaagcac tctgattgac aaatacgatt tatctaattt acacgaaatt   1080
gcttctgggg gcgcacctct ttcgaaagaa gtcggggaag cggttgcaaa acgcttccat   1140
cttccaggga tacgacaagg atatgggctc actgagacta catcagctat tctgattaca   1200
cccgaggggg atgataaacc gggcgcggtc ggtaaagttg ttccattttt tgaagcgaag   1260
gttgtggatc tggataccgg gaaaacgctg ggcgttaatc agagaggcga attatgtgtc   1320
agaggaccta tgattatgtc cggttatgta aacaatccgg aagcgaccaa cgccttgatt   1380
gacaaggatg gatggctaca ttctggagac atagcttact gggacgaaga cgaacacttc   1440
ttcatagttg accgcttgaa gtctttaatt aaatacaaag gatatcaggt ggcccccgct   1500
gaattggaat cgatattgtt acaacacccc aacatcttcg acgcgggcgt ggcaggtctt   1560
cccgacgatg acgccggtga acttcccgcc gccgttgttg ttttggagca cggaaagacg   1620
atgacggaaa aagagatcgt ggattacgtc gccagtcaag taacaaccgc gaaaagttg    1680 cgcggaggag ttgtgtttgt ggacgaagta ccgaaaggtc ttaccggaaa actcgacgca   1740
agaaaaatca gagagatcct cataaaggcc aagaagggcg gaaagtccaa attggtttaa   1800
```